US006251260B1

(12) United States Patent
Heller et al.

(10) Patent No.: US 6,251,260 B1
(45) Date of Patent: Jun. 26, 2001

(54) POTENTIOMETRIC SENSORS FOR ANALYTIC DETERMINATION

(75) Inventors: Adam Heller, Austin, TX (US); Chaim Yarnitzky, Haifa (IL)

(73) Assignee: TheraSense, Inc., Alameda, CA (US)

( * ) Notice: Subject to any disclaimer, the term of this patent is extended or adjusted under 35 U.S.C. 154(b) by 0 days.

(21) Appl. No.: 09/158,973

(22) Filed: Aug. 24, 1998

(51) Int. Cl.[7] ................................................ G01N 27/26
(52) U.S. Cl. ...................... 205/777.5; 205/775; 204/402; 204/403
(58) Field of Search .................................. 204/400, 403, 204/402; 205/775, 777.5

(56) References Cited

U.S. PATENT DOCUMENTS

| | | |
|---|---|---|
| 3,260,656 | 7/1966 | Ross, Jr. . |
| 3,653,841 | 4/1972 | Klein . |
| 3,719,564 | 3/1973 | Lilly, Jr. et al. . |
| 3,776,832 | 12/1973 | Oswin et al. . |
| 3,837,339 | 9/1974 | Aisenberg et al. . |
| 3,972,320 | 8/1976 | Kalman . |
| 3,979,274 | 9/1976 | Newman . |
| 4,008,717 | 2/1977 | Kowarski . |
| 4,016,866 | 4/1977 | Lawton . |
| 4,055,175 | 10/1977 | Clemens et al. . |
| 4,059,406 | 11/1977 | Fleet . |
| 4,076,596 | 2/1978 | Connery et al. . |
| 4,098,574 | 7/1978 | Dappen . |
| 4,100,048 | 7/1978 | Pompei et al. . |
| 4,145,255 * | 3/1979 | Fletcher et al. ..................... 205/778 |
| 4,151,845 | 5/1979 | Clemens . |
| 4,168,205 | 9/1979 | Danninger et al. . |
| 4,172,770 | 10/1979 | Semersky et al. . |
| 4,178,916 | 12/1979 | McNamara . |
| 4,206,755 | 6/1980 | Klein . |
| 4,224,125 | 9/1980 | Nakamura et al. . |
| 4,240,438 | 12/1980 | Updike et al. . |
| 4,240,889 | 12/1980 | Yoda et al. . |
| 4,247,297 | 1/1981 | Berti et al. . |
| 4,271,119 | 6/1981 | Columbus . |
| 4,318,784 | 3/1982 | Higgins et al. . |
| 4,340,458 | 7/1982 | Lerner et al. . |

(List continued on next page.)

FOREIGN PATENT DOCUMENTS

| | | |
|---|---|---|
| 227 029 A3 | 9/1985 | (DD) . |
| 29 03 216 | 8/1979 | (DE) . |
| 4100727 * | 7/1992 | (DE) . |
| 0 048 090 A2 | 3/1982 | (EP) . |
| 0 078 636 A1 | 5/1983 | (EP) . |
| 0 096 288 A1 | 12/1983 | (EP) . |
| 0 125 139 A2 | 11/1984 | (EP) . |
| 0 136 362 A1 | 4/1985 | (EP) . |

(List continued on next page.)

OTHER PUBLICATIONS

Bard, A. et al., "Electrochemical Methods Fundamentals and Applications", *John Wiley & Sons*, Ch. 5.2, p. 143 (1980).

Csöregi, E. et al., "Design and Optimization of a Selective Subcutaneously Implantable Glucose Electrode Based on "Wired" Glucose Oxidase", *Analytical Chemistry*, vol. 67, No. 7, pp. 1240–1244 (Apr. 1, 1995).

Hall, E., "Biosensors", *Prentice Hall Advanced Reference Series Engineering*, Chs. 8 and 9, pp. 216–301 (1991).

(List continued on next page.)

*Primary Examiner*—T. Tung
*Assistant Examiner*—Alex Noguerola
(74) *Attorney, Agent, or Firm*—Merchant & Gould P.C.

(57) ABSTRACT

A potentiometric electrode and method for the determination of an analyte in a sample by linearly correlating potential at the electrode with the concentration of the analyte in the sample.

26 Claims, 7 Drawing Sheets

U.S. PATENT DOCUMENTS

| | | |
|---|---|---|
| 4,356,074 | 10/1982 | Johnson . |
| 4,365,637 | 12/1982 | Johnson . |
| 4,366,033 | 12/1982 | Richter et al. . |
| 4,375,399 | 3/1983 | Havas et al. . |
| 4,384,586 | 5/1983 | Christiansen . |
| 4,392,933 | 7/1983 | Nakamura et al. . |
| 4,401,122 | 8/1983 | Clark, Jr. . |
| 4,404,066 | 9/1983 | Johnson . |
| 4,407,959 | 10/1983 | Tsuji et al. . |
| 4,418,148 | 11/1983 | Oberhardt . |
| 4,420,564 | 12/1983 | Tsuji et al. . |
| 4,427,770 | 1/1984 | Chen et al. . |
| 4,431,004 | 2/1984 | Bessman et al. . |
| 4,436,094 | 3/1984 | Cerami . |
| 4,440,175 | 4/1984 | Wilkins . |
| 4,444,892 | 4/1984 | Malmros . |
| 4,450,842 | 5/1984 | Zick et al. . |
| 4,461,691 | 7/1984 | Frank . |
| 4,469,110 | 9/1984 | Slama . |
| 4,477,314 | 10/1984 | Richter et al. . |
| 4,483,924 | 11/1984 | Tsuji et al. . |
| 4,484,987 | 11/1984 | Gough . |
| 4,522,690 | 6/1985 | Venkatasetty . |
| 4,524,114 | 6/1985 | Samuels et al. . |
| 4,526,661 | 7/1985 | Steckhan et al. . |
| 4,534,356 | 8/1985 | Papadakis . |
| 4,538,616 | 9/1985 | Rogoff . |
| 4,543,955 | 10/1985 | Schroeppel . |
| 4,545,382 | 10/1985 | Higgins et al. . |
| 4,552,840 | 11/1985 | Riffer . |
| 4,560,534 | 12/1985 | Kung et al. . |
| 4,571,292 | 2/1986 | Liu et al. . |
| 4,573,994 | 3/1986 | Fischell et al. . |
| 4,581,336 | 4/1986 | Malloy et al. . |
| 4,595,011 | 6/1986 | Phillips . |
| 4,595,479 | 6/1986 | Kimura et al. . |
| 4,619,754 | 10/1986 | Niki et al. . |
| 4,633,878 | 1/1987 | Bombardieri . |
| 4,637,403 | 1/1987 | Garcia et al. . |
| 4,650,547 | 3/1987 | Gough . |
| 4,654,197 | 3/1987 | Lilja et al. . |
| 4,655,880 | 4/1987 | Liu . |
| 4,655,885 | 4/1987 | Hill et al. . |
| 4,671,288 | 6/1987 | Gough . |
| 4,679,562 | 7/1987 | Luksha . |
| 4,680,268 | 7/1987 | Clark, Jr. . |
| 4,682,602 | 7/1987 | Prohaska . |
| 4,684,537 | 8/1987 | Graetzel et al. . |
| 4,685,463 | 8/1987 | Williams . |
| 4,703,756 | 11/1987 | Gough et al. . |
| 4,711,245 | 12/1987 | Higgins et al. . |
| 4,717,673 | 1/1988 | Wrighton et al. . |
| 4,721,601 | 1/1988 | Wrighton et al. . |
| 4,726,378 | 2/1988 | Kaplan . |
| 4,750,496 | 6/1988 | Reinhart et al. . |
| 4,757,022 | 7/1988 | Shults et al. . |
| 4,758,323 | 7/1988 | Davis et al. . |
| 4,759,371 | 7/1988 | Franetski . |
| 4,759,828 | 7/1988 | Young et al. . |
| 4,764,416 | 8/1988 | Ueyama et al. . |
| 4,776,944 | 10/1988 | Janata et al. . |
| 4,781,798 | 11/1988 | Gough . |
| 4,784,736 | 11/1988 | Lonsdale et al. . |
| 4,795,707 | 1/1989 | Niiyama et al. . |
| 4,805,624 | 2/1989 | Yao et al. . |
| 4,813,424 | 3/1989 | Wilkins . |
| 4,815,469 | 3/1989 | Cohen et al. . |
| 4,820,399 | 4/1989 | Senda et al. . |
| 4,822,337 | 4/1989 | Newhouse et al. . |
| 4,830,959 | 5/1989 | McNeil et al. . |
| 4,832,797 | 5/1989 | Vadgama et al. . |
| 4,840,893 | 6/1989 | Hill et al. . |
| 4,848,351 | 7/1989 | Finch . |
| 4,871,351 | 10/1989 | Feingold . |
| 4,871,440 | 10/1989 | Nagata et al. . |
| 4,890,620 | 1/1990 | Gough . |
| 4,894,137 | 1/1990 | Takizawa et al. . |
| 4,897,162 | 1/1990 | Lewandowski et al. . |
| 4,897,173 | 1/1990 | Nankai et al. . |
| 4,909,908 | 3/1990 | Ross et al. . |
| 4,911,794 | 3/1990 | Parce et al. . |
| 4,919,141 | 4/1990 | Zier et al. . |
| 4,919,767 | 4/1990 | Vadgama et al. . |
| 4,923,586 | 5/1990 | Katayama et al. . |
| 4,924,516 | 5/1990 | Yamaguchi et al. . |
| 4,935,105 | 6/1990 | Churchouse . |
| 4,935,345 | 6/1990 | Guilbeau et al. . |
| 4,936,956 | 6/1990 | Wrighton . |
| 4,938,860 | 7/1990 | Wogoman . |
| 4,942,127 | 7/1990 | Wada et al. . |
| 4,945,045 | 7/1990 | Forrest et al. . |
| 4,950,378 | 8/1990 | Nagata . |
| 4,953,552 | 9/1990 | DeMarzo . |
| 4,968,400 | 11/1990 | Shimomura et al. . |
| 4,970,145 | 11/1990 | Bennetto et al. . |
| 4,974,959 | 12/1990 | Curry . |
| 4,986,271 | 1/1991 | Wilkins . |
| 4,994,167 | 2/1991 | Shults et al. . |
| 5,034,192 | 7/1991 | Wrighton et al. . |
| 5,037,527 | 8/1991 | Hayashi et al. . |
| 5,070,535 | 12/1991 | Hochmair et al. . |
| 5,078,854 | 1/1992 | Burgess et al. . |
| 5,082,550 | 1/1992 | Rishpon et al. . |
| 5,082,786 | 1/1992 | Nakamoto . |
| 5,089,112 | 2/1992 | Skotheim et al. . |
| 5,094,951 | 3/1992 | Rosenberg . |
| 5,096,560 | 3/1992 | Takai et al. . |
| 5,096,836 | 3/1992 | Macho et al. . |
| 5,101,814 | 4/1992 | Palti . |
| 5,108,564 | 4/1992 | Szuminsky et al. . |
| 5,109,850 | 5/1992 | Blanco et al. . |
| 5,120,420 | 6/1992 | Nankai et al. . |
| 5,120,421 | 6/1992 | Glass et al. . |
| 5,126,034 | 6/1992 | Carter et al. . |
| 5,126,247 | 6/1992 | Palmer et al. . |
| 5,130,009 | 7/1992 | Marsoner et al. . |
| 5,133,856 | 7/1992 | Yamaguchi et al. . |
| 5,140,393 | 8/1992 | Hijikihigawa et al. . |
| 5,141,868 | 8/1992 | Shanks et al. . |
| 5,161,532 | 11/1992 | Joseph . |
| 5,165,407 | 11/1992 | Wilson et al. . |
| 5,168,046 | 12/1992 | Hamamoto et al. . |
| 5,174,291 | 12/1992 | Schoonen et al. . |
| 5,185,256 | 2/1993 | Nankai et al. . |
| 5,192,415 | 3/1993 | Yoshioka et al. . |
| 5,192,416 | 3/1993 | Wang et al. . |
| 5,198,367 | 3/1993 | Aizawa et al. . |
| 5,200,051 | 4/1993 | Cozzette et al. . |
| 5,202,261 | 4/1993 | Musho et al. . |
| 5,205,920 | 4/1993 | Oyama et al. . |
| 5,206,145 | 4/1993 | Cattell . |
| 5,208,154 | 5/1993 | Weaver et al. . |
| 5,217,595 | 6/1993 | Smith et al. . |
| 5,227,042 | 7/1993 | Zawodzinski et al. . |
| 5,229,282 | 7/1993 | Yoshioka et al. . |
| 5,250,439 | 10/1993 | Musho et al. . |
| 5,262,035 | 11/1993 | Gregg et al. . |
| 5,262,305 | 11/1993 | Heller et al. . |
| 5,264,103 | 11/1993 | Yoshioka et al. . |
| 5,264,106 | 11/1993 | McAleer et al. . |
| 5,271,815 | 12/1993 | Wong . |

| | | |
|---|---|---|
| 5,272,060 | 12/1993 | Hamamoto et al. . |
| 5,278,079 | 1/1994 | Gubinski et al. . |
| 5,286,362 | 2/1994 | Hoenes et al. . |
| 5,286,364 | 2/1994 | Yacynuch et al. . |
| 5,288,636 | 2/1994 | Pollmann et al. . |
| 5,293,546 | 3/1994 | Tadros et al. . |
| 5,310,885 | 5/1994 | Maier et al. . |
| 5,312,762 * | 5/1994 | Guiseppi-Elie ............... 436/149 |
| 5,320,725 | 6/1994 | Gregg et al. . |
| 5,326,449 | 7/1994 | Cunningham . |
| 5,337,747 | 8/1994 | Neftel . |
| 5,352,348 | 10/1994 | Young et al. . |
| 5,356,786 | 10/1994 | Heller et al. . |
| 5,364,797 | 11/1994 | Olson et al. . |
| 5,368,028 | 11/1994 | Palti . |
| 5,372,133 | 12/1994 | Hogen Esch . |
| 5,378,628 | 1/1995 | Grätzel et al. . |
| 5,380,422 | 1/1995 | Negishi et al. . |
| 5,382,346 | 1/1995 | Uenoyama et al. . |
| 5,387,327 | 2/1995 | Khan . |
| 5,390,671 | 2/1995 | Lord et al. . |
| 5,391,250 | 2/1995 | Cheney, II et al. . |
| 5,393,903 | 2/1995 | Gratzel et al. . |
| 5,395,504 | 3/1995 | Saurer et al. . |
| 5,411,647 | 5/1995 | Johnson et al. . |
| 5,413,690 | 5/1995 | Kost et al. . |
| 5,422,246 | 6/1995 | Koopal et al. . |
| 5,437,973 | 8/1995 | Vadgama et al. . |
| 5,437,999 | 8/1995 | Diebold et al. . |
| 5,478,751 | 12/1995 | Oosta et al. . |
| 5,494,562 | 2/1996 | Maley et al. . |
| 5,496,453 | 3/1996 | Uenoyama et al. . |
| 5,497,772 | 3/1996 | Schulman et al. . |
| 5,501,956 | 3/1996 | Wada et al. . |
| 5,507,288 | 4/1996 | Böcker et al. . |
| 5,508,171 | 4/1996 | Walling et al. . |
| 5,514,253 | 5/1996 | Davis et al. . |
| 5,520,787 | 5/1996 | Hanagan et al. . |
| 5,525,511 | 6/1996 | D'Costa . |
| 5,526,120 | 6/1996 | Jina et al. . |
| 5,531,878 | 7/1996 | Vadgama et al. . |
| 5,552,027 | 9/1996 | Birkle et al. . |
| 5,556,524 | 9/1996 | Albers . |
| 5,565,085 | 10/1996 | Ikeda et al. . |
| 5,567,302 | 10/1996 | Song et al. . |
| 5,568,806 | 10/1996 | Cheney, II et al. . |
| 5,569,186 | 10/1996 | Lord et al. . |
| 5,575,895 | 11/1996 | Ikeda et al. . |
| 5,580,527 | 12/1996 | Bell et al. . |
| 5,582,184 | 12/1996 | Erickson et al. . |
| 5,582,697 | 12/1996 | Ikeda et al. . |
| 5,582,698 | 12/1996 | Flaherty et al. . |
| 5,586,553 | 12/1996 | Halili et al. . |
| 5,589,326 | 12/1996 | Deng et al. . |
| 5,593,852 | 1/1997 | Heller et al. . |
| 5,596,150 | 1/1997 | Arndt et al. . |
| 5,617,851 | 4/1997 | Lipkovker . |
| 5,628,890 | 5/1997 | Carter et al. . |
| 5,650,062 | 7/1997 | Ikeda et al. . |
| 5,651,869 | 7/1997 | Yoshioka et al. . |
| 5,660,163 | 8/1997 | Schulman et al. . |
| 5,670,031 | 9/1997 | Hintsche et al. . |
| 5,680,858 | 10/1997 | Hansen et al. . |
| 5,682,233 | 10/1997 | Brinda . |
| 5,695,623 | 12/1997 | Michel et al. . |
| 5,708,247 | 1/1998 | McAleer et al. . |
| 5,711,861 | 1/1998 | Ward et al. . |
| 5,711,862 | 1/1998 | Sakoda et al. . |
| 5,720,862 | 2/1998 | Hamamoto et al. . |
| 5,727,548 | 3/1998 | Hill et al. . |
| 5,741,211 | 4/1998 | Renirie et al. . |
| 5,741,688 | 4/1998 | Oxenboll et al. . |
| 5,746,217 | 5/1998 | Erickson et al. . |
| 5,770,028 | 6/1998 | Maley et al. . |
| 5,791,344 | 8/1998 | Schulman et al. . |
| 5,804,048 | 9/1998 | Wong et al. . |
| 5,820,570 | 10/1998 | Erickson et al. . |
| 5,830,341 | 11/1998 | Gilmartin . |
| 5,834,224 | 11/1998 | Ruger et al. . |
| 5,837,454 | 11/1998 | Cozzette et al. . |
| 5,842,983 | 12/1998 | Abel et al. . |
| 5,846,702 | 12/1998 | Deng et al. . |
| 5,846,744 | 12/1998 | Athey et al. . |
| 5,857,983 | 1/1999 | Douglas et al. . |
| 5,879,311 | 3/1999 | Duchon et al. . |
| 6,004,441 | 12/1999 | Fujiwara et al. . |
| 6,033,866 | 3/2000 | Guo et al. . |
| 6,071,391 | 6/2000 | Gotoh et al. . |

FOREIGN PATENT DOCUMENTS

| | | |
|---|---|---|
| 0 170 375 A2 | 2/1986 | (EP) . |
| 0 080 304 B1 | 5/1986 | (EP) . |
| 0 184 909 A2 | 6/1986 | (EP) . |
| 0 206 218 A2 | 12/1986 | (EP) . |
| 0 230 472 A1 | 8/1987 | (EP) . |
| 0 241 309 A3 | 10/1987 | (EP) . |
| 0 245 073 A2 | 11/1987 | (EP) . |
| 0 278 647 A2 | 8/1988 | (EP) . |
| 0 286 084 A2 | 10/1988 | (EP) . |
| 0 359 831 A1 | 3/1990 | (EP) . |
| 0 368 209 A1 | 5/1990 | (EP) . |
| 0 390 390 A1 | 10/1990 | (EP) . |
| 0 400 918 A1 | 12/1990 | (EP) . |
| 0 453 283 A1 | 10/1991 | (EP) . |
| 0 470 290 A1 | 2/1992 | (EP) . |
| 0 255 291 B1 | 6/1992 | (EP) . |
| 0 127 958 B2 | 4/1996 | (EP) . |
| 0 781 406 B1 | 5/1998 | (EP) . |
| 1394 171 | 5/1975 | (GB) . |
| 2 073 891 | 10/1981 | (GB) . |
| 2 154 003 | 8/1985 | (GB) . |
| 2 204 408 | 11/1988 | (GB) . |
| 54-41191 | 4/1979 | (JP) . |
| 55-10581 | 1/1980 | (JP) . |
| 55-10583 | 1/1980 | (JP) . |
| 55-10584 | 1/1980 | (JP) . |
| 55-12406 | 1/1980 | (JP) . |
| 56-163447 | 12/1981 | (JP) . |
| 57-70448 | 4/1982 | (JP) . |
| 60-173457 | 9/1985 | (JP) . |
| 60-173458 | 9/1985 | (JP) . |
| 60-173459 | 9/1985 | (JP) . |
| 61-90050 | 5/1986 | (JP) . |
| 62-85855 | 4/1987 | (JP) . |
| 62-114747 | 5/1987 | (JP) . |
| 63-58149 | 3/1988 | (JP) . |
| 63-128252 | 5/1988 | (JP) . |
| 63-139246 | 6/1988 | (JP) . |
| 63-294799 | 12/1988 | (JP) . |
| 63-317758 | 12/1988 | (JP) . |
| 1-114746 | 5/1989 | (JP) . |
| 1-114747 | 5/1989 | (JP) . |
| 1-134244 | 5/1989 | (JP) . |
| 1-156658 | 6/1989 | (JP) . |
| 2-62958 | 3/1990 | (JP) . |
| 2-120655 | 5/1990 | (JP) . |
| 2-287145 | 11/1990 | (JP) . |
| 2-310457 | 12/1990 | (JP) . |
| 3-26956 | 2/1991 | (JP) . |
| 3-28752 | 2/1991 | (JP) . |
| 3-202764 | 9/1991 | (JP) . |
| 5-72171 | 3/1993 | (JP) . |

| | | |
|---|---|---|
| 5-196595 | 8/1993 | (JP). |
| 1281988 A1 | 1/1987 | (SU). |
| WO 85/05119 | 11/1985 | (WO). |
| WO 89/08713 | 9/1989 | (WO). |
| WO 90/05300 | 5/1990 | (WO). |
| WO 91/04704 | 4/1991 | (WO). |
| WO 92/13271 | 8/1992 | (WO). |
| WO 94/20602 | 9/1994 | (WO). |
| WO 94/27140 | 11/1994 | (WO). |
| WO 95/02817 | 1/1995 | (WO). |
| WO 97/00441 | 1/1997 | (WO). |
| WO 97/18464 | 5/1997 | (WO). |
| WO 97/19344 | 5/1997 | (WO). |
| WO 97/42882 | 11/1997 | (WO). |
| WO 97/42883 | 11/1997 | (WO). |
| WO 97/42886 | 11/1997 | (WO). |
| WO 97/42888 | 11/1997 | (WO). |
| WO 97/43962 | 11/1997 | (WO). |
| WO 99/08106 | 2/1999 | (WO). |
| WO 99/30152 | 6/1999 | (WO). |

OTHER PUBLICATIONS

Harsányi, E.G. et al, "The Behaviour of the Silver Precipitate–Based Ion–Selective Electrode in the Low Concentration Range", *Analytica Chimica Acta*, vol. 161, pp. 333–341 (1984).

Nagy, A. et al., "Investigation of a novel chronopotentiometric detection method using a redox mediator modified carbon electrode", *Analytica Chimica Acta*, vol. 310, pp. 241–249 (1995).

Schmidtke, D. et al., "Measurement and modeling of the transient difference between blood and subcutaneous glucose concentrations in the rat after injection of insulin", *Proc. Natl. Acad. Sci. USA*. vol. 95, pp. 294–299 (Jan. 1998).

Tomlinson, K. et al., "Potentiometric System for the Continuous Determination of Low Levels of Chloride in High-purity Power Station Waters", *The Analyst*, vol. 102, No. 1210, pp. 1–8 (Jan. 1977).

Wagner, J.G. et al., "Continuous amperometric monitoring of glucose in a brittle diabetic chimpanzee with a miniature subcutaneous electrode", *Proc. Natl. Acad. Sci USA*, vol. 95, pp. 6379–6382 (May 1998).

Yarnitzky, C. et al., "Linear Dependence of the Potential of "Wired" Glucose Oxidase Electrodes on the Concentration of glucose", *J. Phys. Chem. B*, vol. 102, No. 49, pp. 10057–10061 (Oct., 1998).

Abruña, H. D. "Rectifying Interfaces Using Two–Layer Films of Electrochemically Polymerized Vinylpyridine and Vinylbipyridine Complexes of Ruthenium and Iron on Electrodes," *J. Am. Chem. Soc.*, 103(1):1–5 (Jan. 14, 1981).

Albery, W. J. et al., "Amperometric enzyme electrodes. Part II. Conducting salts as electrode materials for the oxidation of glucose oxidase," *J. Electroanal. Chem. Interfacial Electrochem.*, 194(2) (1 page—Abstract only) (1985).

Albery, W. J. et al., "Amperometric Enzyme Electrodes," *Phil. Trans. R. Soc. Lond.* B316:107–119 (1987).

Alcock, S. J. et al., "Continuous Analyte Monitoring to Aid Clinical Practice," *IEEE Engineering in Medicine and Biology*, 319–325 (1994).

Anderson, L. B. et al., "Thin–Layer Electrochemistry: Steady–State Methods of Studying Rate Processes," *J. Electroanal. Chem.*, 10:295–305 (1965).

Bartlett, P. N. et al., "Covalent Binding of Electron Relays to Glucose Oxidation," *J. Chem. Soc. Chem. Commun.*, 1603–1604 (1987).

Bartlett, P. N. et al., "Modification of glucose oxidase by tetrathiafulvalene," *J. Chem. Soc., Chem. Commun.*, 16 (1 page—Abstract only) (1990).

Bartlett, P. N. et al., "Strategies for the Development of Amperometric Enzyme Electrodes," *Biosensors*, 3:359–379 (1987/88).

Bobbioni–Harsch, E. et al., "Lifespan of subcutaneous glucose sensors and their performances during dynamic glycaemia changes in rats," *J. Biomed. Eng.* 15:457–463 (1993).

Brandt, J. et al., "Covalent attachment of proteins to polysaccharide carriers by means of benzoquinone," *Biochim. Biophys. Acta*, 386(1) (1 page Abstract only) (1975).

Brownlee, M. et al., "A Glucose–Controlled Insulin–Delivery System: Semisynthetic Insulin Bound to Lectin", *Science*, 206(4423):1190–1191 (Dec. 7, 1979).

Cass, A.E.G. et al., "Ferricinum Ion As An Electron Acceptor for Oxidase–Reductases," *J. Electroanal. Chem.*, 190:117–127 (1985).

Cass, A.E.G. et al., "Ferrocene–Mediated Enzyme Electrode for Amperometric Determination of Glucose", *Anal. Chem.*, 56(4):667–671 (Apr. 1984).

Castner, J. F. et al., "Mass Transport and Reaction Kinetic Parameters Determined Electrochemically for Immobilized Glucose Oxidase," *Biochemisty*, 23(10):2203–2210 (1984).

Claremont, D.J. et al., "Biosensors for Continuous In Vivo Glucose Monitoring", *IEEE Engineering in Medicine and Biology Society 10th Annual International Conference*, New Orleans, Louisiana, 3 pgs. (Nov. 4–7, 1988).

Chen, C.Y. et al., "A Biocompatible Needle–Type Glucose Sensor Based on Platinum–Electroplated Carbon Electrode", *Applied Biochemistry and Biotechnology*, 36:211–226 (1992).

Chen, C.Y. et al., "Amperometric Needle–Type Glucose Sensor based on a Modified Platinum Electrode with Diminished Response to Interfering Materials", *Analytica Chimica Acta*, 265:5–14 (1992).

Clark, L.C. et al., "Differential Anodic Enzyme Polarography for the Measurement of Glucose", *Oxygen Transport to Tissue: Instrumentation, Methods, and Physiology*, 127–133 (1973).

Clark, L.C., Jr. et al., "Electrode Systems for Continuous Monitoring in Cardiovascular Surgery," *Annals New York Academy of Sciences*, pp. 29–45 (1962).

Clarke, W. L., et al., "Evaluating Clinical Accuracy of Systems for Self–Monitoring of Blood Glucose," *Diabetes Care*, 10(5):622–628 (Sep.–Oct. 1987).

Csöregi, E. et al., "Design, Characterization, and One–Point in Vivo Calibration of a Subcutaneously Implanted Glucose Electrode," *Anal. Chem.* 66(19):3131–3138 (Oct. 1, 1994).

Csöregi, E. et al., "On–Line Glucose Monitoring by Using Microdialysis Sampling and Amperometric Detection Based on "Wired" Glucose Oxidase in Carbon Paste," *Mikrochim. Acta*. 121:31–40 (1995).

Davis, G., "Electrochemical Techniques for the Development of Amperometric Biosensors", *Biosensors*, 1:161–178 (1985).

Degani, Y. et al., "Direct Electrical Communication between Chemically Modified Enzymes and Metal Electrodes. 1. Electron Transfer from Glucose Oxidase to Metal Electrodes via Electron Relays, Bound Covalently to the Enzyme,"*J. Phys. Chem.*, 91(6):1285–1289 (1987).

Degani, Y. et al., "Direct Electrical Communication between Chemically Modified Enzymes and Metal Electrodes. 2. Methods for Bonding Electron–Transfer Relays to Glucose Oxidase and D–Amino–Acid Oxidase," *J. Am. Chem. Soc.,* 110(8):2615–2620 (1988).

Degani, Y. et al., "Electrical Communication between Redox Centers of Glucose Oxidase and Electrodes via Electrostatically and Covalently Bound Redox Polymers," *J. Am. Chem. Soc.,* 111:2357–2358 (1989).

Denisevich, P. et al., "Unidirectional Current Flow and Charge State Trapping at Redox Polymer Interfaces on Bilayer Electrodes: Principles, Experimental Demonstration, and Theory," *J. Am. Chem. Soc.,* 103(16):4727–4737 (1981).

Dicks, J.M., "Ferrocene modified polypyrrole with immobilised glucose oxidase and its application in amperometric glucose microbiosensors," *Ann. Biol. clin.,* 47:607–619 (1989).

Engstrom, R.C., "Electrochemical Pretreatment of Glassy Carbon Electrodes", *Anal. Chem.,* 54(13):2310–2314 (Nov. 1982).

Engstrom, R.C. et al., "Characterization of Electrochemically Pretreated Glassy Carbon Electrodes", *Anal. Chem.,* 56(2):136–141 (Feb. 1984).

Ellis, C. D., "Selectivity and Directed Charge Transfer through an Electroactive Metallopolymer Film," *J. Am. Chem. Soc.,* 103(25):7480–7483 (1981).

Fischer, H. et al., "Intramolecular Electron Transfer Mediated by 4,4'–Bipyridine and Related Bridging Groups", *J. Am. Chem. Soc.,* 98(18):5512–5517 (Sep. 1, 1976).

Foulds, N.C. et al., "Enzyme Entrapment in Electrically Conducting Polymers," *J. Chem. Soc., Faraday Trans 1.,* 82:1259–1264 (1986).

Foulds, N.C. et al., "Immobilization of Glucose Oxidase in Ferrocene–Modified Pyrrole Polymers," *Anal. Chem.,* 60(22):2473–2478 (Nov. 15, 1988).

Frew, J.E. et al., "Electron–Transfer Biosensors", *Phil. Trans. R. Soc. Lond.,* B316:95–106 (1987).

Gernet, S. et al., "Fabrication and Characterization of a Planar Electrochemical Cell and Its Application as a Glucose Sensor", *Biosensors & Actuators,* 18:59–70 (1989).

Gorton, L. et al., "Selective detection in flow analysis based on the combination of immobilized enzymes and chemically modified electrodes," *Analytica Chimica Acta.,* 250:203–248 (1991).

Gregg, B. A. et al., "Cross–Linked Redox Gels Containing Glucose Oxidase for Amperometric Biosensor Applications," *Analytical Chemistry,* 62(3):258–263 (Feb. 1, 1990).

Gregg, B.A. et al., "Redox Polymer Films Containing Enzymes. 1. A Redox–Conducting Epoxy Cement: Synthesis, Characterization, and Electrocatalytic Oxidation of Hydroquinone," *J. Phys. Chem.,* 95(15):5970–5975 (1991).

Hale, P.D. et al., "A New Class of Amperometric Biosensor Incorporating a Polymeric Electron–Transfer Mediator," *J. Am. Chem. Soc.,* 111(9):3482–3484 (1989).

Harrison, D.J. et al., "Characterization of Perfluorosulfonic Acid Polymer Coated Enzyme Electrodes and a Miniaturized Integrated Potentiostat for Glucose Analysis in Whole Blood", *Anal. Chem.,* 60(19):2002–2007 (Oct. 1, 1988).

Hawkridge, F. M. et al., "Indirect Coulometric Titration of Biological Electron Transport Components," *Analytical Chemistry,* 45(7):1021–1027 (Jun. 1973).

Heineman, W.R. et al., "Measurement of Enzyme $E^{o'}$ Values by Optically Transparent Thin Layer Electrochemical Cells", *Analytical Chemistry,* 47(1):79, 82–84 (Jan. 1975).

Heineman, W.R. "Spectro–electro–chemistry", *Analytical Chemistry,* 50(3):390–392, 394, 396, 398, 400, 402 (Mar. 1978).

Heller, A., "Amperometric biosensors based on three–dimensional hydrogel–forming epoxy networks," *Sensors and Actuators B,* 13–14:180–183 (1993).

Heller, A., "Electrical Wiring of Redox Enzymes," *Acc. Chem. Res.,* 23(5):129–134 (1990).

Ianniello, R.M. et al. "Immobilized Enzyme Chemically Modified Electrode as an Amperometric Sensor", *Anal. Chem.,* 53(13):2090–2095 (Nov. 1981).

Ianniello, R.M. et al., "Differential Pulse Voltammetric Study of Direct Electron Transfer in Glucose Oxidase Chemically Modified Graphite Electrodes", *Anal. Chem.,* 54:(7):1098–1101 (Jun. 1981).

Ikeda, T. et al., "Glucose oxidase–immoblized benzoquinone–carbon paste electrode as a glucose sensor," *Agric. Biol. Chem.,* 49(2) (1 page—Abstract only) (1985).

Johnson, J. M. et al., "Potential–Dependent Enzymatic Activity in an Enzyme Thin–Layer Cell," *Anal. Chem.* 54:1377–1383 (1982).

Johnson K. W. et al., "In Vivo Evaluation of an Electroenzymatic Glucose Sensor Implanted in Subcutaneous Tissue", *Biosensors & bioelectronics* 7:709–714 (1992).

Johnson, K.W., "Reproducible Electrodeposition of Biomolecules for the Fabrication of Miniature Electroenzymatic Biosensors", *Sensors and Actuators B Chemical,* B5:85–89 (1991).

Jösson, G. et al., "An Amperometric Glucose Sensor Made by Modification of a Graphite Electrode Surface With Immobilized Glucose Oxidase and Adsorbed Mediator", *Biosensors,* 1:355–368 (1985).

Josowicz, M. et al., "Electrochemical Pretreatment of Thin Film Platinum Electrodes", *J. Elecrochem. Soc.,* 135(1):112–115 (Jan. 1988).

Katakis, I. et al., "Electrostatic Control of the Electron Transfer Enabling Binding of Recombinant Glucose Oxidase and Redox Polyelectrolytes," *J. Am. Chem. Soc.,* 116(8):3617–3618 (1994).

Katakis, I. et al., "L–α–Glycerophosphate and L–Lactate Electrodes Based on the Electrochemical "Wiring" of Oxidases," *Analytical Chemistry,* 64(9): 1008–1013 (May 1, 1992).

Kenausis, G. et al., "Wiring' of glucose oxidase and lactate oxidase within a hydrogel made with poly(vinyl pyridine) complexed with $[Os(4,4'-dimethoxy-2,2'-bipyridine)_2Cl]^{+/2+}$," *J. Chem. Soc., Faraday Trans.,* 92(20):4131–4136 (1996).

Kondo, T. et al., "A Miniature Glucose Sensor, Implantable in the blood Stream", *Diabetes Care,* 5(3):218–221 (May-Jun. 1982).

Kulys, J. et al., "Mediatorless peroxidase electrode and preparation of bienzyme sensors," *Bioelectrochemisty and Bioenergetics,* 24:305–311 (1990).

Lager, W. et al., "Implantable Electrocatalytic Glucose Sensor," *Horm. Metab. Res.,* 26: 526–530 (Nov. 1994).

Lee, J. et al., "A New Glucose Sensor using Microporous Enzyme Membrane", *Sensors and Actuators,* B3:215–219 (1991).

Lewandowski, J.J. et al., "Evaluation of a Miniature Blood Glucose Sensor", *Trans Am Soc Artif Intern Organs*, XXXIV: 255–258 (1988).

Lindner, E. et al. "Flexible (Kapton–Based) Microsensor Arrays of High Stability for Cardiovascular Applications",*J. Chem. Soc.Faraday Trans.*, 89(2):361–367 (Jan. 21, 1993).

Maidan, R. et al., "Elimination of Electrooxidizable Interferant–Produced Currents in Amperometric Biosensor," *Analytical Chemistry*, 64(23):2889–2896 (Dec. 1, 1992).

Mann–Buxbaum, E. et al, "New Microminiaturized Glucose Sensors Using Covalent Immoblilization Techniques", *Sensors and Actuators*, B1:518–522 (1990).

Mastrototaro, J.J. et al., "An Electroenzymatic Glucose Sensor Fabricated on a Flexible Substrate", *Sensors and Biosensors B Chemical*, B5:139–144 (1991).

Matthews, D.R., et al., "An Amperometric Needle–Type Glucose Sensor Tested in Rats and Man", *Original Articles*, pp. 248–252 (1988).

McKean et al., "A telemetry–Instrumentation System for Chronically Implanted Glucose and Oxygen Sensors",*IEEE Transactions of Biomedical Engineering*, 35(7):526–532 (Jul. 1988).

McNeil, C. J. et al., "Thermostable Reduced Nicotinamide Adenine Dinucleotide Oxidase: Application to Amperometric Enzyme Assay," *Anal. Chem.*, 61(1):25–29 (Jan. 1, 1989).

Miyawaki, O. et al., "Electrochemical and Glucose Oxidase Coenzyme Activity of Flavin Adenine Dinucleotide Covalently Attached to Glassy Carbon at the Adenine Amino Group", *Biochimica et Biophysica Acta*, 838:60–68 (1985).

Moatti–Sirat, D. et al., "Evaluating in vitro and in vivo the inteference of ascorbate and acetaminophen on glucose detection by a needle–type glucose sensor," *Biosensors & Bioelectronics*, 7(5):345–352 (1992).

Moatti–Sirat, D. et al., "Reduction of acetaminophen interference in glucose sensors by a composite Nafion membrane: demonstration in rats and man," *Diabetologia*, 37(6) (1 page—Abstract only) (Jun. 1994).

Moatti–Sirat, D. et al., "Towards continuous glucose monitoring: in vivo evaluation of a miniaturized glucose sensor implanted for several days in rat subcutaneous tissue," *Diabetologia*, 35(3) (1 page—Abstract only) (Mar. 1992).

Moser, I. et al., "Advanced Immobilization and Protein Techniques on thin Film Biosensors", *Sensors and Actuators*, B7:356–362 (1992).

Moussy, F. et al., "Performance of Subcutaneously Implanted Needle–Type Glucose Sensors Employing a Novel Trilayer Coating", *Anal. Chem.*, 65:2072–2077 (1993).

Nagy, G. et al., "A New Type of Enzyme Electrode: The Ascorbic Acid Eliminator Electrode," *Life Sciences*, 31(23):2611–2616 (1982).

Nakamura, S. et al., "Effect of Periodate Oxidation on the Structure and Properties of Glucose Oxidase," *Biochimica et Biophysica Acta.*, 445:294–308 (1976).

Narazimhan, K. et al., "p–Benzoquinone activation of metal oxide electrodes for attachment of enzymes," *Enzyme Microb. Technol.* 7(6) (1 page—Abstract only) (1985).

Ohara, T. J. et al., "Glucose Electrodes Based on Cross–Linked $[Os(bpy)_2Cl]^{+/2+}$ Complexed Poly(1–vinylimadazole) Films," *Analytical Chemistry*, 65(23):3512–3516 (Dec. 1, 1993).

Ohara, T. J., "Osmium bipyridyl Redox Polymers Used in Enzyme Electrodes," *Platinum Metals Rev.*, 39(2):54–62 (Apr. 1995).

Ohara T. J. et al., ""Wired" Enzyme Electrodes for Amperometric Determination of Glucose or Lactate in the Presence of Intefering Substances," *Analytical Chemistry*, 66(15):2451–2457 (Aug. 1, 1994).

Olievier, C. N. et al., "In vivo Measurement of Carbon Dioxide Tension with a Miniature Electrode," *Pflugers Arch.* 373:269–272 (1978).

Paddock, R. et al., "Electrocatalytic reduction of hydrogen peroxide via direct electron transfer from pyrolytic graphite electrodes to irreversibly adsorbed cytochrome c peroxidase," *J. Electroanal. Chem.*, 260:487–494 (1989).

Palleschi, G. et al., "A Study of Interferences in Glucose Measurements in Blood by Hydrogen Peroxide Based Glucose Probes", *Anal. Biochem.*, 159:114–121 (1986).

Palleschi, G. et al. "Ideal Hydrogen Peroxide–Based Glucose Sensor", *Applied Biochemistry and Biotechnology*, 31:21–35 (1991).

Pankratov, I. et al., "Sol–gel derived renewable–surface biosensors," *Journal of Electroanalytical Chemistry*, 393:35–41 (1995).

Pathak, C. P. et al., "Rapid Photopolymerization of Immunoprotective Gels in Contact with Cells and Tissue," *J. Am. Chem. Soc.*, 114(21):8311–8312 (1992).

Pickup, J. et al., "Potentially–implantable, amperometric glucose sensors with mediated electron transfer: improving the operating stability," *Biosensors*, 4(2) (1 page—Abstract only) (1989).

Pishko, M. V. et al., "Amperometric Glucose Microelectrodes Prepared Through Immobilization of Glucose Oxidase in Redox Hydrogels",*Anal. Chem.*, 63(20):2268–2272 (Oct. 15, 1991).

Poitout, V. et al., "A glucose monitoring system for on line estimation in man of blood glucose concentration using a miniaturized glucose sensor implanted in the subcutaneous tissue and a wearable control unit," *Diabetolgia*, 36(7) (1 page—Abstract only) (Jul. 1993).

Poitout, V. et al., "Calibration in dogs of a subcutaneous miniaturized glucose sensor using a glucose meter for blood glucose determination," *Biosensors & Bioelectronics*, 7:587–592 (1992).

Poitout, V. et al., "In vitro and in vivo evaluation in dogs of a miniaturized glucose sensor," *ASAIO Transactions*, 37(3) (1 page—Abstract only) (Jul.–Sep. 1991).

Pollak, A. et al., "Enzyme Immobilization by Condensation Copolymerization into Cross–Linked Polyacrylamide Gels," *J. Am. Chem. Soc.*, 102(20):6324–6336 (1980).

Pons, B. S. et al., "Application of Deposited Thin Metal Films as Optically Transparent Electrodes for Internal Reflection Spectometric Observation of Electrode Solution Interfaces", *Analytical Chemistry*, 39(6):685–688, (May 1967).

Reach, G. et al., "A Method for Evaluating in vivo the Functional Characteristics of Glucose Sensors", *Biosensors* 2:211–220 (1986).

Reach, G. et al., "Can Continuous Glucose Monitoring Be Used for the Treatment of Diabetes?" *Analytical Chemistry*, 64(6):381–386 (Mar. 15, 1992).

Rebrin, K. et al., "Automated Feedback Control of Subcutaneous Glucose Concentration in Diabetic Dogs", *Diabetologia*, 32(8):573–576 (Aug. 1989).

Sasso, S. V. et al., "Electropolymerized 1,2–Diaminobenzene as a Means to Prevent Interferences and Fouling and to Stabilize Immobilized Enzyme in Electrochemical Biosensors", *Anal. Chem.*, 62(11):1111–1117 (Jun. 1, 1990).

Schalkhammer, T. et al, "Electrochemical Glucose Sensors on Permselective Non–conducting Substituted Pyrrole Polymers", *Sensors and Actuators,* B4:273–281 (1991).

Scheller, F. et al., "Enzyme electrodes and their application," *Phil. Trans. R. Soc. Lond.,* B 316:85–94 (1987).

Shichiri, M. et al., "Glycaemic Control in Pancreatetomized Dogs with a Wearable Artificial Endocrine Pancreas", *Diabetologia*, 24(3):179–184 (Mar. 1983).

Shigeru, T. et al, "Simultaneous Determination of Glucse and 1,5–= Anydroglucitol", *Chemical Abstracts,* 111:394 (1989).

Sittampalam, G. et al., "Surface–Modified Electrochemical Detector for Liquid Chromatography", *Anal. Chem.,* 55(9):1608–1610 (Aug. 1983).

Soegijoko, S. et al., *Horm. Metabl. Res., Suppl. Ser,* 12 (1 page—Abstract only) (1982).

Sprules, S. D. et al., "Evaluation of a New Disposable Screen–Printed Sensor Strip for the Measurement of NADH and Its Modification to Produce a Lactate Biosensor Employing Microliter Volumes," *Electroanalysis,* 8(6):539–543 (1996).

Sternberg, F. et al., "Calibration Problems of Subcutaneous Glucosensors when Applied "In–Situ" in Man," *Horm. metalb. Res,* 26:523–525 (1994).

Sternberg, R. et al., "Covalent Enzyme Coupling on Cellulose Acetate Membranes for Glucose Sensor Development," *Analytical Chemistry,* 60(24):2781–2786 (Dec. 15, 1988).

Suekane, M., "Immobilization of glucose isomerase," *Zeitschrift für Allgemeine Mikrobiologie,* 22(8):565–576 (1982).

Tarasevich, M.R. "Bioelectrocatalysis", *Comprehensive Treatise of Electrochemistry,* 10 (Ch. 4):231–295 (1985).

Taylor, C. et al., "Wiring ' of glucose oxidase within a hydrogel made with polyvinyl imidazole complexed with [(Os–4,4'–dimethoxy–2,2'–bipyridine)Cl]$^{+/2+}$," *Journal of Electroanalytical Chemistry,* 396:511–515 (1995).

Trojanowicz, M. et al., "Enzyme Entrapped Polypyrrole Modified Electrode for Flow–Injection Determination of Glucose," *Biosensors & Bioelectronics,* 5:149–156 (1990).

Turner, A.P.F. et al., "Diabetes Mellitus: Biosensors for Research and Management", *Biosensors,* 1:85–115 (1985).

Turner, R. F. B. et al., "A Biocompatible Enzyme Electrode for Continuous in vivo Glucose Monitoring in Whole Blood," *Sensors and Actuators,* B1(1–6):561–564 (Jan. 1990).

Umaha, M., "Protein–Modified Electrochemically Active Biomaterial Surface," *U.S. Army Research Office Report,* (12 pages) (Dec. 1988).

Urban, G. et al., "Miniaturized Thin–Film Biosensors Using Covalently Immobilized Glucose Oxidase", *Biosensors & Bioelectronics,* 6(7):555–562 (1991).

Velho, G. et al., "Strategies for calibrating a subcutaneous glucose sensor," *Biomed. Biochin. Acta,* 48(11/12):957–964 (1989).

Von Woedtke, T. et al., "In Situ Calibration of Implanted Electrochemical Glucose Sensors," *Biomed. Biochim. Acta,* 48(11/12):943–952 (1989).

Vreeke, M. S. et al., "Chapter 15: Hydrogen Peroxide Electrodes Based on Electrical Connection of Redox Centers of Various Peroxidases to Electrodes through a Three–Dimensional Electron–Relaying Polymer Network," *Diagnostic Biosensor Polymers,* 7 pgs. (Jul. 26, 1993).

Vreek, M. et al., "Hydrogen Peroxide and β–Nicotinamide Adenine Dinucleotide Sensing Amperometric Electrodes Based on Electrical Connection of Horseradish Peroxidase Redox Centers to Electrodes through a Three–Dimensional Electron Relaying Polymer Network," *Analytical Chemistry,* 64(24):3084–3090 (Dec. 15, 1992).

Wang, J. et al., "Activation of Glassy Carbon Electrodes by Alternating Current Electrochemical Treatment", *Analytica Chimica Acta,* 167:325–334 (Jan. 1985).

Wang, J. et al., "Amperometric biosensing of organic peroxides with peroxidase–modified electrodes," *Analytica Chimica Acta.* 254:81–88 (1991).

Wang, J. et al., "Screen–Printable Sol–Gel Enzyme–Containing Carbon Inks," *Analytical Chemistry,* 68(15):2705–2708 (Aug. 1, 1996).

Wang, J. et al., "Sol–Gel–Derived Metal–Dispersed Carbon Composite Amperometric Biosensors," *Electroanalysis,* 9(1):52–55 (1997).

Williams, D.L. et al., "Electrochemical–Enzymatic Analysis of Blood Glucose and Lactate", *Anal. Chem.,* 42(1):118–121 (Jan. 1970).

Yabuki, S. et al., "Electro–conductive Enzyme Membrane," *J. Chem. Soc. Chem. Commun,* 945–946 (1989).

Yamasaki, Y., "The Development of a Needle–Type Glucose Sensor for Wearable Artificial Endocrine Pancreas", *Medical Journal of Osaka University,* vol. 35, No. 1–2, pp. 24–34 (Sep. 1994).

Yang, L. et al., "Determination of Oxidase Enzyme Substrates Using Cross–Flow Thin–Layer Amperometry," *Electroanaylsis,* 8(8–9):716–721 (1996).

Yao, S.J. et al., "The Interference of Ascorbate and Urea in Low–Potential Electrochemical Glucose Sensing", *Proceedings of the Twelfth Annual International Conference of the IEEE Engineering in Medicine and Biology Society,* 12(2):487–498 (Nov. 1–4, 1990).

Yao, T. et al., "A Chemically–Modified Enzyme Membrane Electrode As An Amperometric Glucose Sensor," *Analytica Chimica Acta.,* 148:27–33 (1983).

Ye, L. et al., "High Current Density "Wired" Quinoprotein Glucose Dehydrogenase Electrode," *Anal. Chem.,* 65(3):238–241 (Feb. 1, 1993).

Yildiz, A., "Evaluation of an Improved Thin–Layer Electrode", *Analytical Chemistry,* 40(7):1018–1024 (Jun. 1968).

Zamzow, K. et al., New Wearable Continuous Blood Glucose Monitor (BGM) and Artificial Pancreas (AP), *Diabetes,* 39:5A(20) (May 1990).

* cited by examiner

POTENTIOMETRIC SENSORS FOR ANALYTIC DETERMINATION

FIELD OF THE INVENTION

The invention is generally related to a method of determining a concentration of an analyte in a solution through measuring a potential, the potential varying about linearly with the concentration of the analyte. The method of the invention enables reproducible electrochemical determination of analyte concentration with electrodes having a variety of sizes, in cells having a variety of volumes, while resolving small changes in the concentration of the analyte.

BACKGROUND OF THE INVENTION

The concentration of glucose and other chemicals and biochemicals can be monitored electrochemically through potentiometry, amperometry or coulometry. (See , for example, Hall, E. A. H., *Biosensors*, Prentice Hall, N.J., 1991, Chapters 8 and 9). While amperometry requires knowledge of the area of the electrode and coulometry requires knowledge of the liquid volume analyzed, potentiometry does not require such knowledge. In high volume manufacturing, control of electrode dimensions or microcell volumes is of essence, respectively in amperometric or coulometric biosensors, but not in potentiometric ones. The disadvantage of potentiometric devices has been that their output scaled with the logarithm of the concentration of the analyte rather than with its concentration. Consequently, the penalty in potentiometry has been the inability to resolve small changes in concentrations.

Potentiometric assays, unlike amperometric or coulometric ones, do not require accurate definition and knowledge of the area of the measuring electrode or microcell volume. Large scale manufacturing of devices for potentiometric assay, for example of strips for single-use potentiometric self-monitoring of blood glucose concentrations by diabetic patients, would therefore not require the tight control of size, microroughness, or microcell volume that is required for large scale manufacturing of available amperometric, chronoamperometric or chronocoulometric strips. However, the potential increases or decreases usually approximately linearly with the logarithm of the analyte concentration, while the current in amperometry and the charge in coulometry increases usually approximately linearly with the analyte concentration. For this reason, changes in glucose concentration were previously better resolved by amperometry or coulometry than by potentiometry. Also, in large arrays of sensors, such as those produced, for example, through combinatorial processes to have large numbers of different elements, it is necessary to compare the magnitude of signals from different sensing elements. Better resolution of differences between elements of an array, in which not all elements are necessarily of the same size, is enabled through potentiometry, if the potentiometrically derived signal scales about linearly with the concentration of the analyte rather than with the logarithm of its concentration.

SUMMARY OF THE INVENTION

A method has now been developed that allows the realization of the advantages of both the electrode area or cell volume independence of potentiometry, and the linear, rather than logarithmic, scaling of the signal with analyte concentration. These advantages are simultaneously realized when the electrode is coated with a resistive, but nevertheless electron-conducting, film. The analyte is electrooxidized or electroreduced on or in this film.

In one example of a glucose sensor, a working electrode includes a film that has a redox polymer that electrically connects ("wires") reaction centers of an enzyme, such as glucose oxidase, catalyzing the electrooxidation of glucose at the electrode. After a potential pulse is applied to the "wired" enzyme electrode so that the electrode-bound redox centers are electrooxidized, the floating electrode potential decays to a value that varies linearly with the concentration of glucose. It is believed that the dependence of this potential on analyte concentration is linear when the potential is dominated by the ohmic resistance of the redox polymer film, not by the overpotential of electron transfer from the electrode to the film.

The instant invention thus provides a potentiometric analyte sensor and method for determination of an analyte in a sample using a potentiometric assay system, where the potential varies approximately linearly with the concentration of the analyte.

The above summary of the present invention is not intended to describe each disclosed embodiment or every implementation of the present invention. The Figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
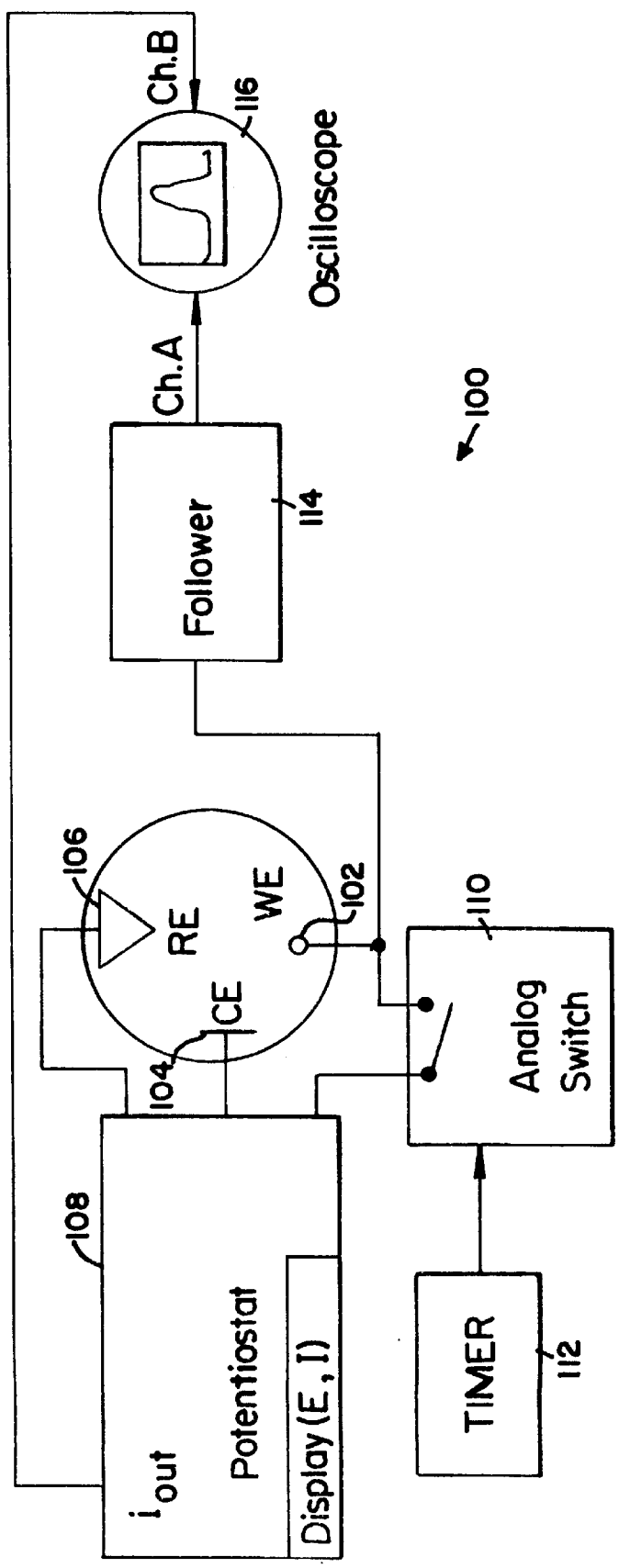
FIG. 1 is a block diagram, showing the components of an exemplary embodiment of a potentiometric measurement system of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

It has been discovered that the concentration of an electrooxidizable or electroreducible analyte can be determined by measuring a potential; and that the change in potential is about proportional to the change in the concentration of the analyte, the potential decreasing or increasing about linearly with the concentration of the analyte. Such linearity is achieved when the electrode on which the analyte is electrooxidized or electroreduced is coated with a film that (a) catalyzes the electrooxidation or the electroreduction of an analyte; and (b) allows the transport of electrons or electron vacancies, but is nevertheless resistive.

As used herein, the term "resistive" means the diffusivity of electrons in the solution-contacted film on the electrode is typically not less than about $10^{-12}$ cm$^2$sec$^{-1}$ and not greater than about $10^{-5}$ cm$^2$sec$^{-1}$, and preferably is between about $10^{-10}$ cm$^2$sec$^{-1}$ and $10^{-7}$ cm$^2$sec$^{-1}$.

The preferred films are redox polymers, including, for example, redox centers that are covalently, coordinately, or electrostatically bound to a polymer. The redox polymers can be organic, inorganic, or mixed polymers with redox centers capable of exchanging electrons with each other. Useful redox polymers are described in the copending U.S. patent applications entitled "Rapid Amperometric Verification of PCR Amplification of DNA", and "Electrochemical Affinity Assay", filed on the same date as the instant application. Transport of electrons through a film having multiple redox centers can take place, by redox conduction, where an electron or electron vacancy is transferred from one redox center to another.

The assay of the invention is performed in a sequence of steps, in one of which a potential pulse is applied to the working electrode, for example by closing a switch between the working electrode and a potentiostat, and potential sufficing to electroreduce or electrooxidize a component of the film, particularly redox centers of the film. This reduction or oxidation step is then followed by another step, where the application of the potential is stopped, for example by opening a switch, then allowing the potential of the electrode to decay or to rise. The potential is then measured, either continuously or repeatedly, and the final potential, which is asymptotically approached as the measured potential decays or rise, is estimated from the measurements. This sequence of steps may be repeated as many times as necessary to confirm the value of the final potential. Alternatively, when the decay or rise behavior of the potential is already known for a particular coated working electrode, the assay can be performed by a single potential measurement, the potential being measured after a known time period elapsed following the opening of the circuit, whereupon application of a potential to the electrode is stopped.

The final electrode potential approached after removal of the applied potential is typically approximately linearly related to the concentration of the analyte. In the specific case of a polymer film having redox centers and an enzyme catalyzing the oxidation of glucose, the potential typically scales approximately linearly with the glucose concentration, not with the logarithm of the concentration.

The measuring system and assay method of the invention thus differ from earlier potentiometric systems in two ways. The working electrode is coated with an electron-conducting redox polymer, catalyzing the electrooxodation or electroreduction of the analyte; and the electronic system monitors the relaxation of the potential following, not during the application of a potential pulse, i.e., when an external potential is no longer applied to the electrode.

When the catalytic redox polymer film on the electrode is in the reduced state, after being exposed at open circuit to the electroxidizable analyte containing solution, then closing of the circuit and poising the electrode at an oxidizing potential results in the flow of a large, rapidly decaying electrooxidation current. The decay characteristics of the current resemble those modeled by a modified Cottrell equation. (See, for example, Bard and Faulkner, "*Electrochemical Methods: Fundamentals and Applications*", Wiley, 1980, page 143). When the switch is opened, and the potential of the film on the electrode is allowed to relax, the potential that is approached is that potential where the inbound flux of electrons through the film, inbound meaning from its solution side to its electrode side, equals the outbound flux of electrons from the electrode to the solution side. According to the hypothesis, the inbound electron flux is determined, in the case of a film on or in which the analyte is electrooxidized, by the analyte flux to the film, which increases linearly with the analyte concentration in the solution. The outbound electron flux can be determined either by the kinetics of electron transfer between the electrode and the film, in which case the flux may vary about exponentially with the potential; or it can be determined not by the electron transfer kinetics but by the resistance of the film, meaning the transport of electrons through the film, in which case the flux varies, according to Ohm's law, linearly with the potential. It is in the latter case that the potential varies approximately linearly with the concentration of the analyte.

According to this hypothesis, the preferred film useful in the potentiometric sensors and methods of the invention:

(a) catalyzes the electrooxidation or electroreduction of analyte;

(b) exchanges electrons or electron vacancies rapidly with the electrode; and (c) is resistive so that the current is controlled by the transport of electrons or electron vacancies through the film, not by the exchange of electrons or electron vacancies between the film and the electrode.

Figure 6:
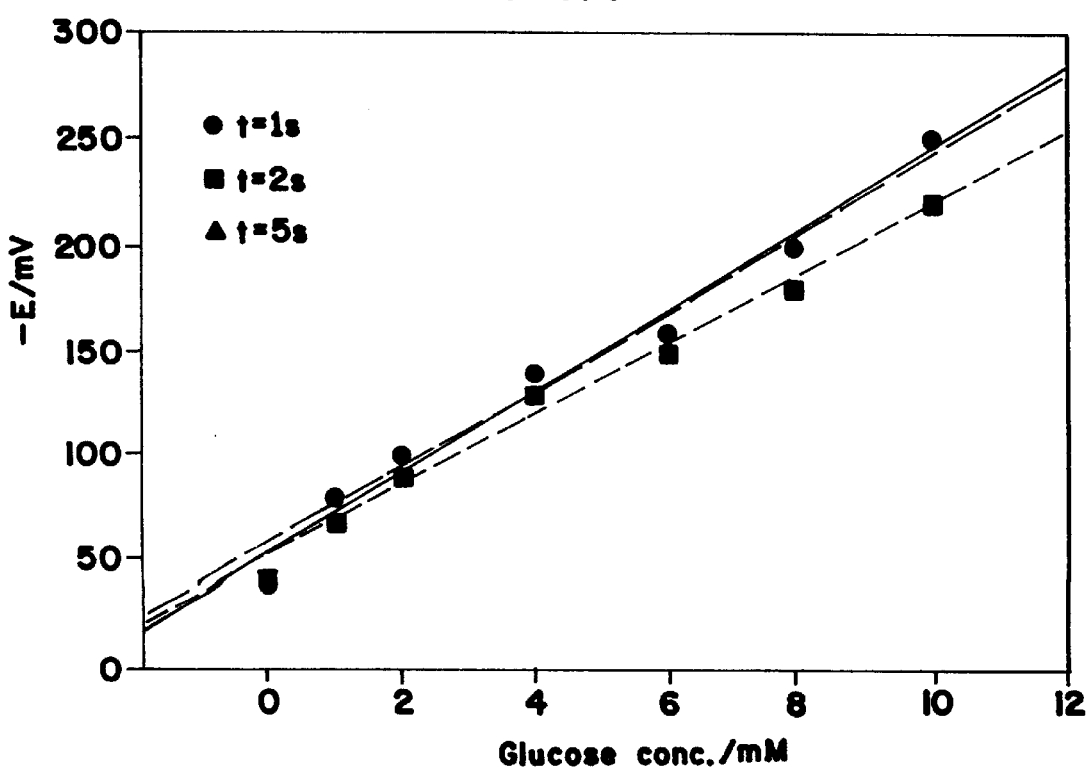
FIG. 6 is a graph showing the dependence of the potential, measured at the end of an open-circuit period of 50 seconds, on the glucose concentration. 300 mV (Ag/AgCl) potential pulses were applied for t=1, 2 or 5 seconds. Conditions and the electrode were as described above for FIG. 2.
Figure 8:
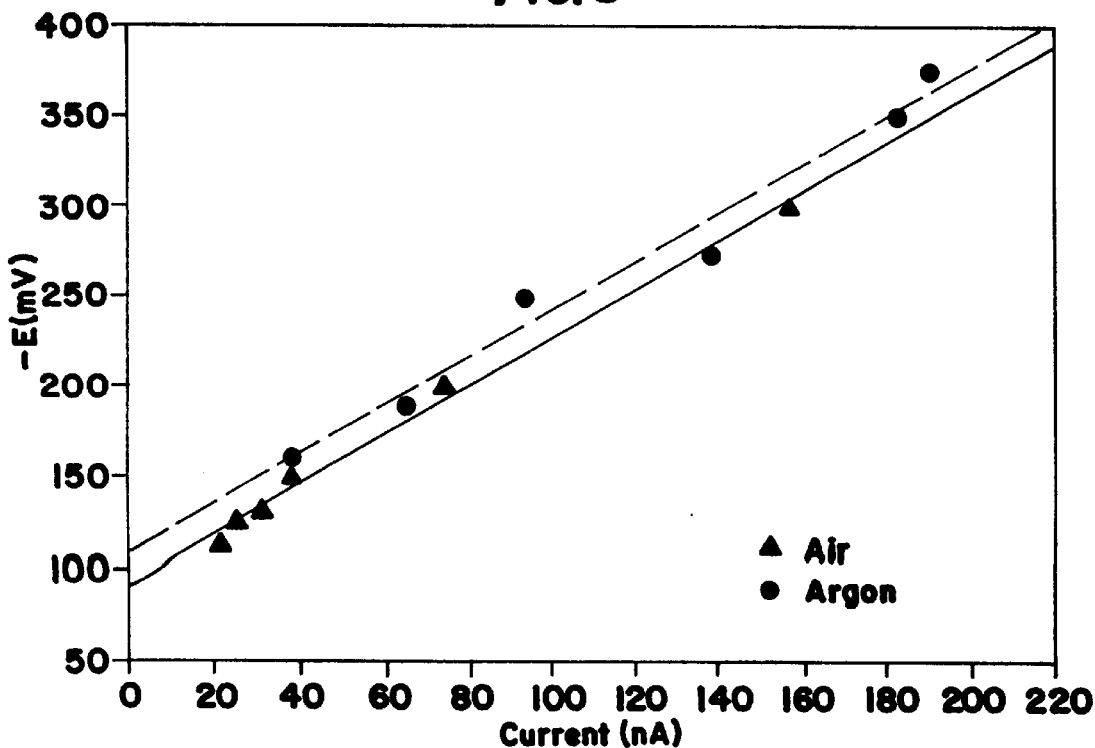
FIG. 8 is a graph showing the dependence of the potential, at the end of a τ=50 seconds open circuit period following a t=1 second potential pulse, on the current at the end of the 1 second pulse. Conditions and the electrode were as described above for FIG. 2.
Figure 9A:
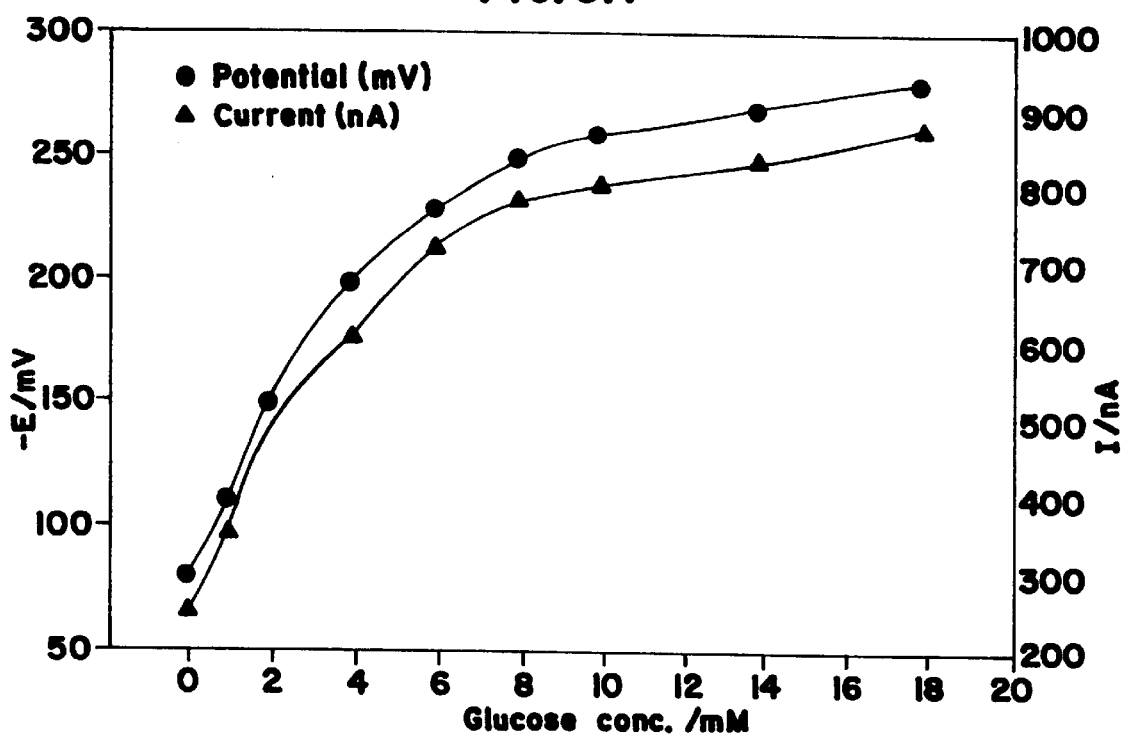
FIGS. 9A and 9B are graphs showing the dependence of the current and of the potential on the glucose concentrations and dependence of the potential on a current for a 5 mm diameter printed carbon electrode. τ=50 seconds; t=1 second. Currents were measured at the end of the potential pulse. Conditions were as above for FIG. 2. The area of the electrode was about 0.2 cm$^2$, about 400 times larger than the area of the gold electrode used to generate the data in FIGS. 2 to 8.
Figure 9B:
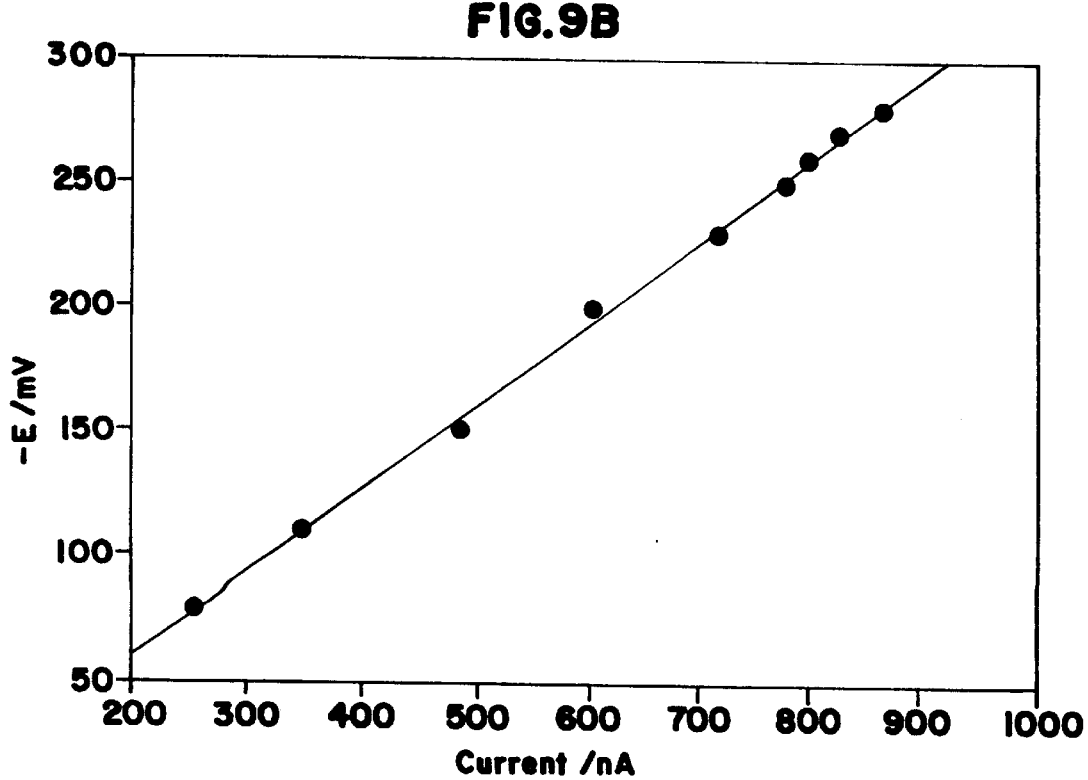

FIGS. 6, 8 and 9 show that in the case of working electrodes coated with a redox polymer film that includes glucose oxidase, the potential approached by the electrode following application of a potential pulse varies approximately linearly with the glucose concentration and the glucose electrooxidation current, decreasing as the current increases. Such linear variation is not observed in the absence of the film, as shown in FIG. 10. The linear dependence holds for electrodes of different structure and size (FIGS. 6 and 9). Because the current varies linearly with the glucose concentration, the potential also varies linearly with the glucose concentration in deoxygenated solutions and at concentrations below the apparent Michaelis constant of the enzyme electrode.

According to the hypothesis detailed above, the current/potential relationship can be controlled either by the electrode kinetics, i.e. the flux of electrons between the electrode and the film; or by the flux of electrons through the film, i.e. the resistance of the films to electron transport. The flux of electrons between the film and the electrode is typically represented by the Butler-Volmer or Tafel equations, the current increasing exponentially with the overpotential. This is the case for an uncoated platinum electrode in a $K_3Fe(CN)_6$ solution (FIG. 10). The flux of electrons through the redox polymer film, however, obeys Ohm's law, the current increasing linearly with the potential across the resistive film. A condition for linear dependence of the potential on the current, which is the rate of electron generation through glucose electrooxidation, is that transport of electrons between the electrode and the polymer be fast relative to the rate of electron transport through the polymer.

At the molecular level, the following model may explain the linear dependence of the potential on current or glucose concentration. The potential, to which the redox polymer film relaxes after application of a pulse of sufficient potential to electrooxidize remote redox centers, is that potential where the outbound and inbound electron currents are equal. In an electrode coated with a redox-polymer which connects reaction centers of glucose oxidase to an electrode, the inbound current equals (in an oxygen depleted solution and below the apparent Michaelis constant of the electrode) twice the glucose flux, the electrooxidation reaction being glucose→gluconolactone+$2H^+$+$2e^-$. The outbound electron current, when dominated not by the overpotential for electron transport from the electrode to the redox polymer but by the resistance of the polymer, is defined by Ohm's law, varying linearly, not exponentially, with potential. At equilibrium the electrode poises itself at a potential that is sufficiently reducing to create a counter-flux of outbound electrons, the counter flux equaling the inbound glucose-generated electron flux. When the flux of electrons is limited by the diffusion of electrons through the redox polymer, then the potential scales linearly with current or glucose flux. The implication of the linear dependence of the potential on the analyte, e.g. glucose, concentration is that an area and cell-volume independent potentiometric analyte sensor can be made. The sensor is capable of resolving small changes in analyte. This eases the manufacture, for example of single-use strips for glucose monitoring, used in the management of diabetes.

One embodiment of a potentiometric sensor 100 is illustrated in FIG. 1. The potentiometric sensor 100 includes a working electrode 102 (WE), a counter electrode 104 (CE), and a reference electrode 106 (RE). In other embodiments, the reference electrode may be omitted or a counter/reference electrode used. The working electrode 102 typically has a film (not shown) coating the surface of the electrode. The film includes redox centers that can transfer electrons either directly or indirectly between the analyte and the working electrode 102. The film is often formed using a redox polymer, as described above. The film may also include a catalyst, such as an enzyme, the catalyzes the electrooxidation or electroreduction of the analyte.

A potential-producing device 108, such as, for example, a potentiostat, is provided and coupled to the working electrode 102, counter electrode 104, and reference electrode 106. The potential-producing device 108 is generally capable of providing a desired potential across the working and counter electrodes 102, 104.

A switch 110 is provided between the working electrode 102 and the potential-producing device 108 to open and close a circuit between these two components. The switch may be, for example, an analog switch, a Hall effect switch, a reed switch, a transistor, or another semiconductor device or circuit component. The switch 110 may be operated manually and/or by another circuit component, such as a timer circuit 112.

The working, counter, and reference electrodes 102, 104, 106 are coupled to a detector to measure a potential at the working electrode 102 after the switch 110 has been opened. An exemplary detector includes an analog or digital oscilloscope 114 and a follower circuit 116. Other detectors can also be used. In addition, a processor (not shown) may be included to process and/or record the signals from the electrodes 102, 104, 106.

In operation, the switch 110 between the working electrode 102 and the potential-producing device 108 is closed to allow the potential-producing device 108 to apply a first potential at the working electrode 102. The first potential is typically applied for 1 second or more, although shorter time periods may also be used. The first potential electrooxidizes or electroreduces the redox centers in the film on the working electrode 102. The first potential can be applied for a period of time ranging from, for example, 1 to 10 seconds, although longer and shorter potentials can be used. In some embodiments, the potential is applied to so that at least 75%, preferably, 90%, and, more preferably, 99%, of the redox centers are in a desired oxidation state.

The switch 110 is then opened to break the connection between the working electrode 102 and the potential-producing device 108. The analyte than proceeds to electroreduce (or electrooxidize) the previously electrooxidized (or electroreduced) redox centers, optionally, using the catalyst (e.g., enzyme). The potential at the working electrode 102 begins to change, as described above, to asymptotically approach a second potential that is typically an approximately linear function of the concentration of the analyte. The first potential and the asymptotic approach to the second potential can be monitored by the detector. Alternatively, the detector may measure a single point at a predetermined time after the switch 110 is opened to determine the concentration of the analyte.

EXAMPLES

The invention may be better understood by reference to the following examples, which are not intended to limit the scope of the invention.

Example 1

Materials, Solutions and Electrodes

The materials, reagents, buffers, and miniature electrodes used were similar to those described in J. G. Wagner et.al., Proceedings of the National Academy of Sciences, 95, 6379–6382 (1998); See also Schmidtke, et.al, *Proceedings of the National Academy of Science*, 95, 294–299 (1998); Csöregi et.al., *Analytical Chemistry*, 67, 1240–1244 (1995). Specifically, the gold electrodes were of 250 $\mu$m diameter and were recessed at 90 $\mu$m depth in a polyimide sleeve. They were coated with three layers: a transduction or sensing layer, consisting of a water-containing redox polymer in which glucose oxidase was immobilized and through which the reaction centers of the enzyme were electrically connected ("wired") to the electrode; a mass-transport limiting layer; and a biocompatible solution-contacting hydrogel. The glucose oxidase "wiring" polymer (i.e., redox polymer) was {poly[1-vinylimidazole) osmium(4,4'-dimethylbipyridine)$_2$ Cl]}$^{+/2+}$ where one imidazole in 13 was osmium complexed. The redox polymer was crosslinked using poly(ethylene glycol) diglycidyl ether.

A much larger, 5 mm diameter, printed carbon electrodes on Mylar™ were prepared with a sensing layer identical with that of the miniature gold electrodes. Their mass transport limiting layer consisted of a Poretics® polycarbonate membrane with 0.01 $\mu$m pores (Poretics catalog #11001).

Example 2

The System

The system's block diagram is shown in FIG. 1. Its elements were a built miniature low-power potentiostat with a display; a follower; a timer-activated analog switch (SCL 4066); a standard 3-electrode electrochemical cell; and an oscilloscope (HP 54501A) for continuous monitoring of the current and the potential. Chronoamperograms were recorded while the switch was closed. The follower-sensed potential of the working electrode was virtually zero, the working electrode being connected to a current-to-voltage converter. All potentials were measured versus ground. Chronopotentiograms were recorded after opening the switch.

Example 3

Potentiometric Determination of Glucose

Figure 2A:
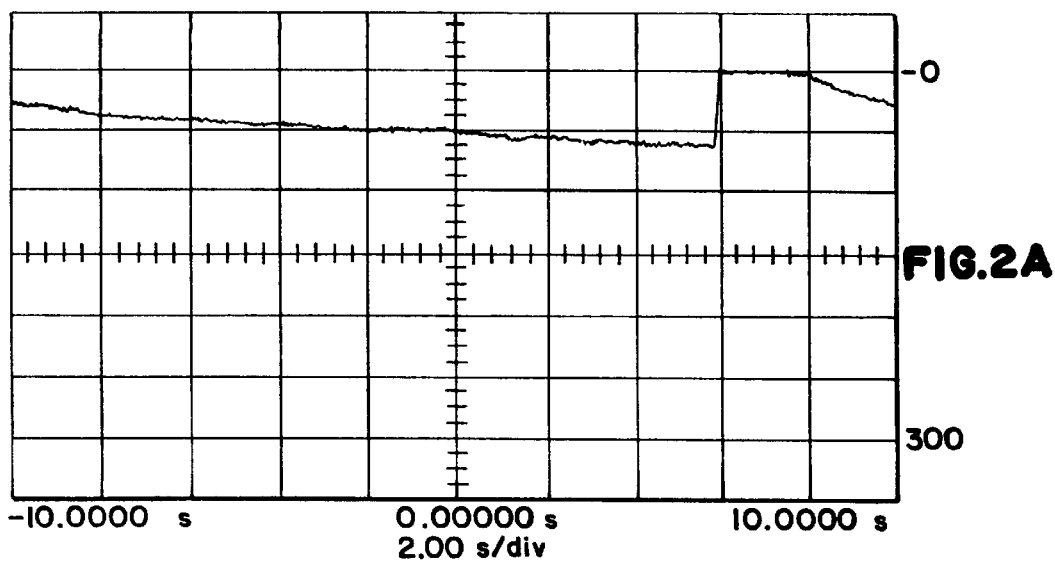
FIGS. 2A–2C are graphs showing the time dependence of the potential of the working electrode. The switch was opened and the potential was allowed to float for $\tau=20$ seconds; next the switch was closed and 300 mV vs. Ag/AgCl was applied for t=2 seconds; then the circuit was again opened for $\tau=20$ seconds. Glucose concentrations were 0 mM (FIG. 2A); 8 mM (FIG. 2B); and 16 mM (FIG. 2C) under reaction conditions of 37° C.; 0.15 M NaCl; pH 7.4; and 0.02 M phosphate buffer; the solution was stirred and air exposed. The electrode is the tip of a 0.25 mm diameter gold wire, the area of which is about $5\times10^{-4}$ cm$^2$.
Figure 2B:
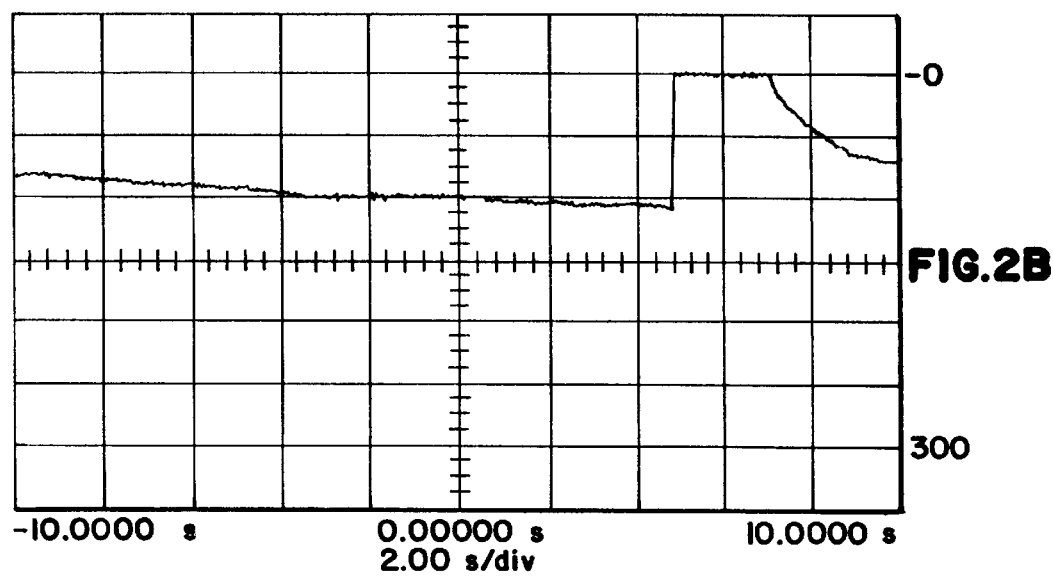
Figure 2C:
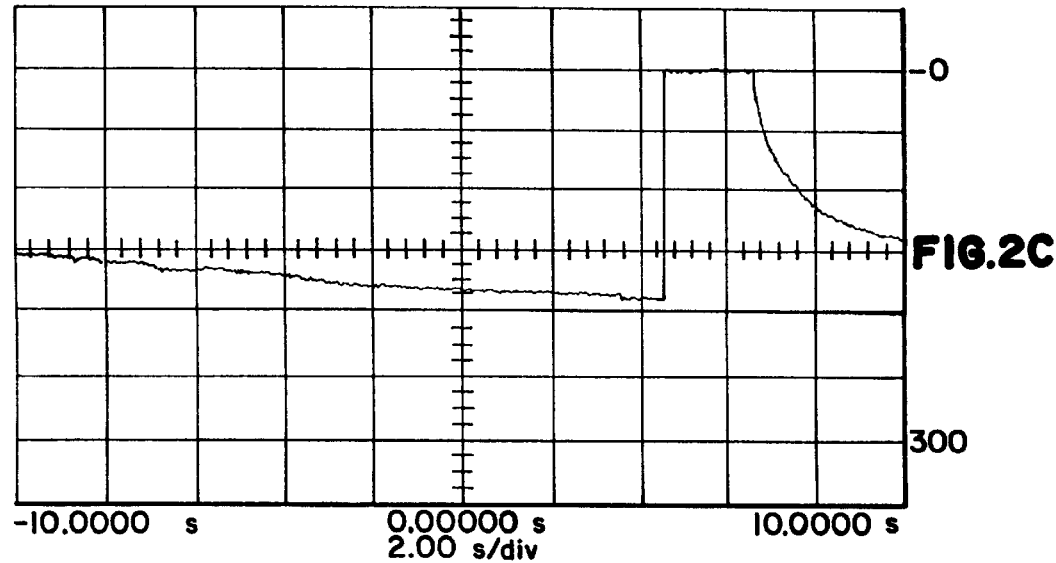

The electrode used in this experiment was the 250 $\mu$m diameter coated gold electrode described for Example 1. FIG. 2 shows the observed chronopotentiograms at (a) 0, (b) 8 and (c) 16 mM glucose concentrations. The cycles of the chronopotentiograms involved two steps, repeated as necessary: In the first step of $\tau$=20 seconds duration the switch was open and the working electrode potential was allowed to float. In the second step, the switch was closed and a potential of +300 mV versus the Ag/AgCl reference electrode was applied for t=2 seconds; the switch was then opened again and the cycle was repeated. As seen in FIG. 2, both the decay characteristics of the potential after opening the switch and the potential observed 20 seconds after the switch was opened depended on the concentration of glucose. The potential measured 20 seconds after opening the switch did not change significantly when the transiently applied potential was raised from 300 mV to 400 mV vs. Ag/AgCl.

Figure 3:
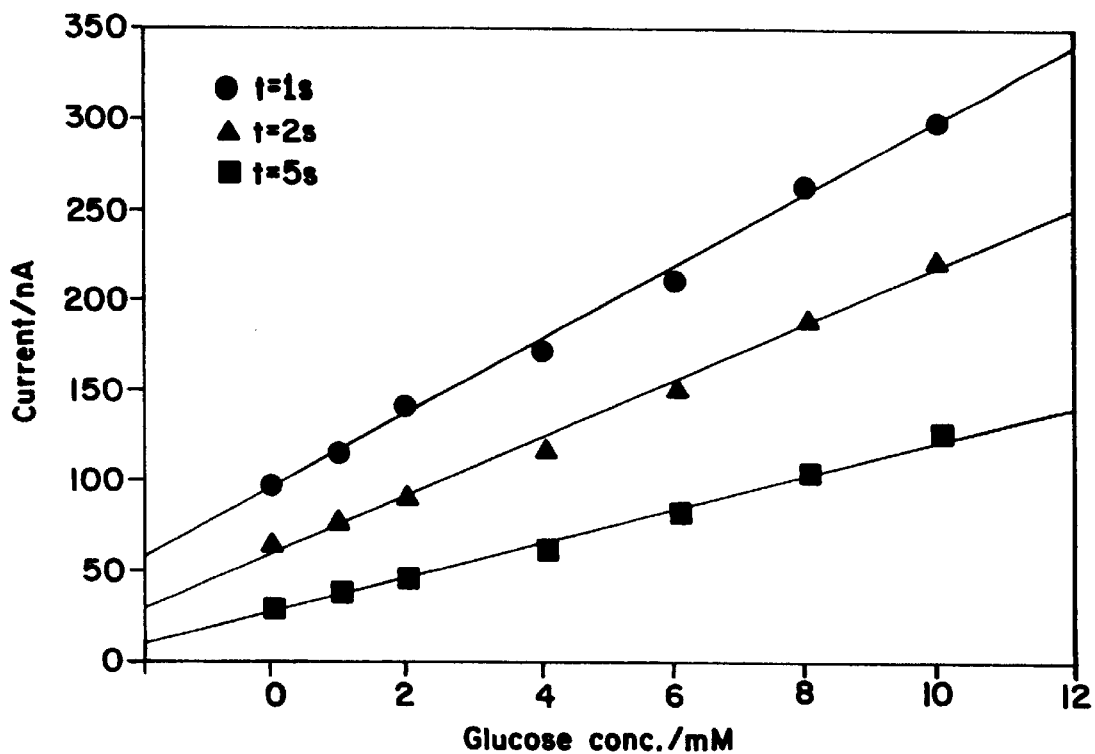
FIG. 3 is a graph showing the dependence of the current measured at the end of the period during which the 300 mV (Ag/AgCl) potential was applied on the glucose concentration. The currents following application of t=1, 2 and 5 seconds potential pulses are shown. Conditions and electrode were as described above for FIG. 2.
Figure 4:
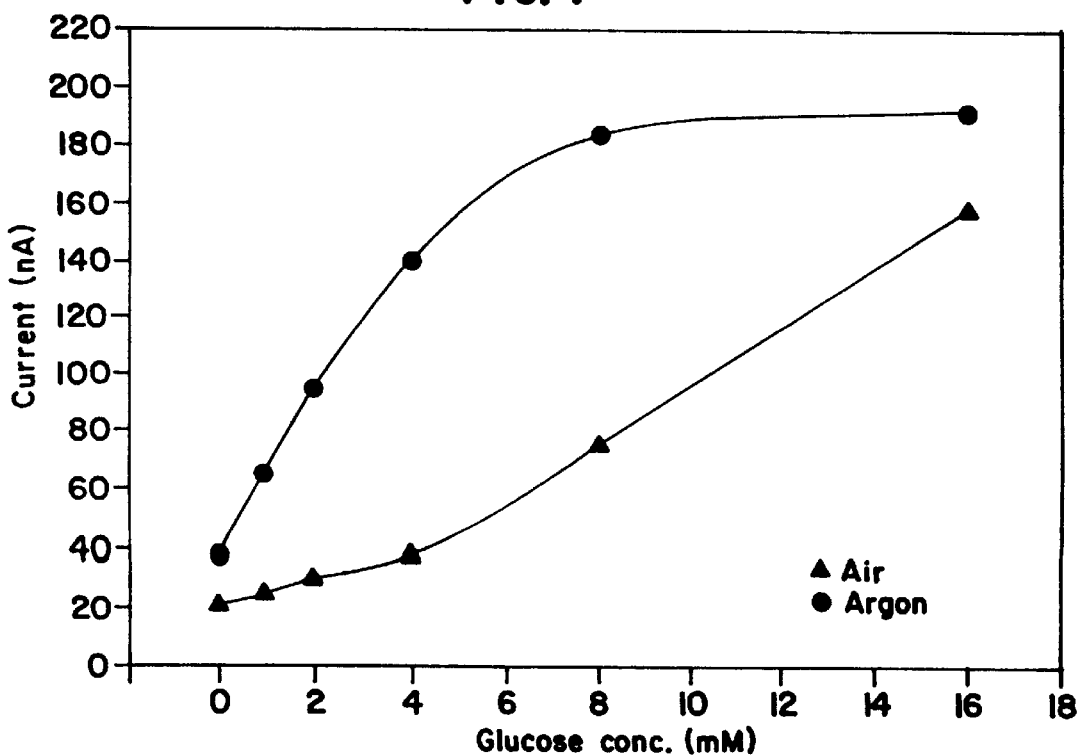
FIG. 4 is a graph showing the effect of deoxygenation of the solution on the amperometric calibration curves. Conditions and the electrode are the same as described above for FIG. 3; with applied potential pulses of t=1 second duration.

FIG. 3 shows three amperometric calibration curves. The currents were measured at the end of the 1, 2 or 5 seconds periods during which the switch was closed, a 300 mV (Ag/AgCl) potential being applied. The currents depended on the oxygenation of the solutions, increasing when the solution was swept with argon (FIG. 4).

Figure 5:
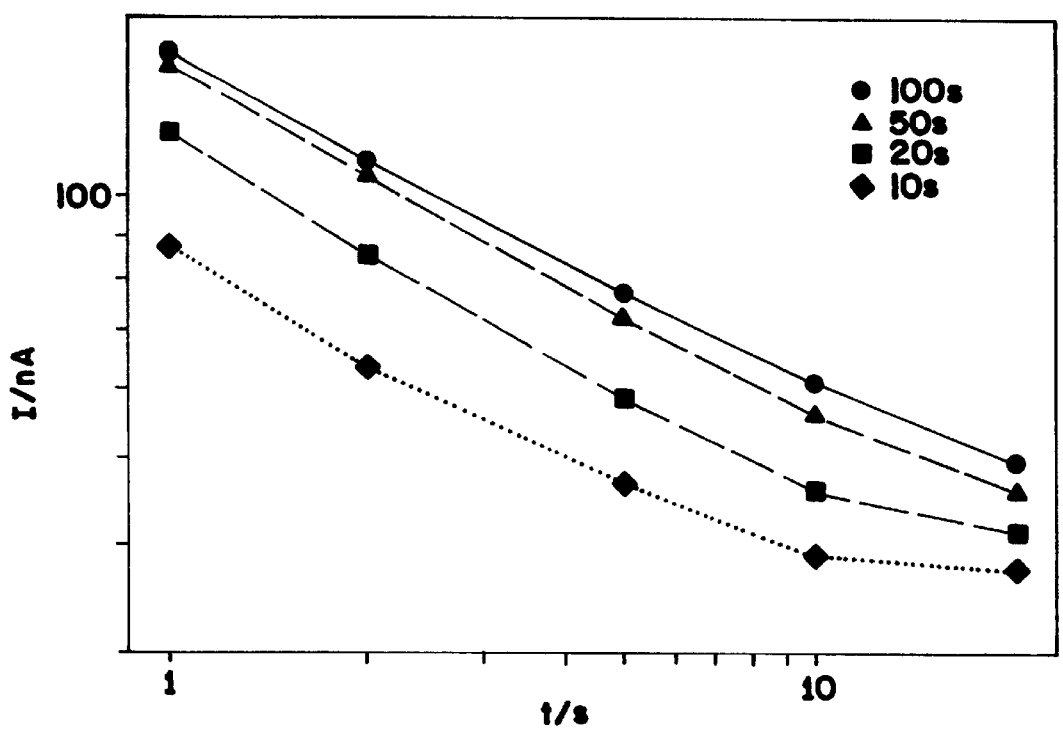
FIG. 5 is a graph showing the dependence of the current at the end of the potential pulse on pulse duration (t) and on the interval ($\tau$) between the pulses. Note that both the ordinate and the abscissa are logarithmic. The dashed line at the bottom represents the ideal relationship for a diffusion-controlled process (log I −0.5 log t). Conditions and the electrode were as described above for FIG. 2.

FIG. 5 shows, for 25 mM glucose concentration on a log/log chart, the dependence of the current (i) on the periods $\tau$ and t. For a diffusion controlled process logI –0.5 log $\tau$. The theoretical –0.5 slope is shown as a dashed line at the bottom of the figure.

Figure 7:
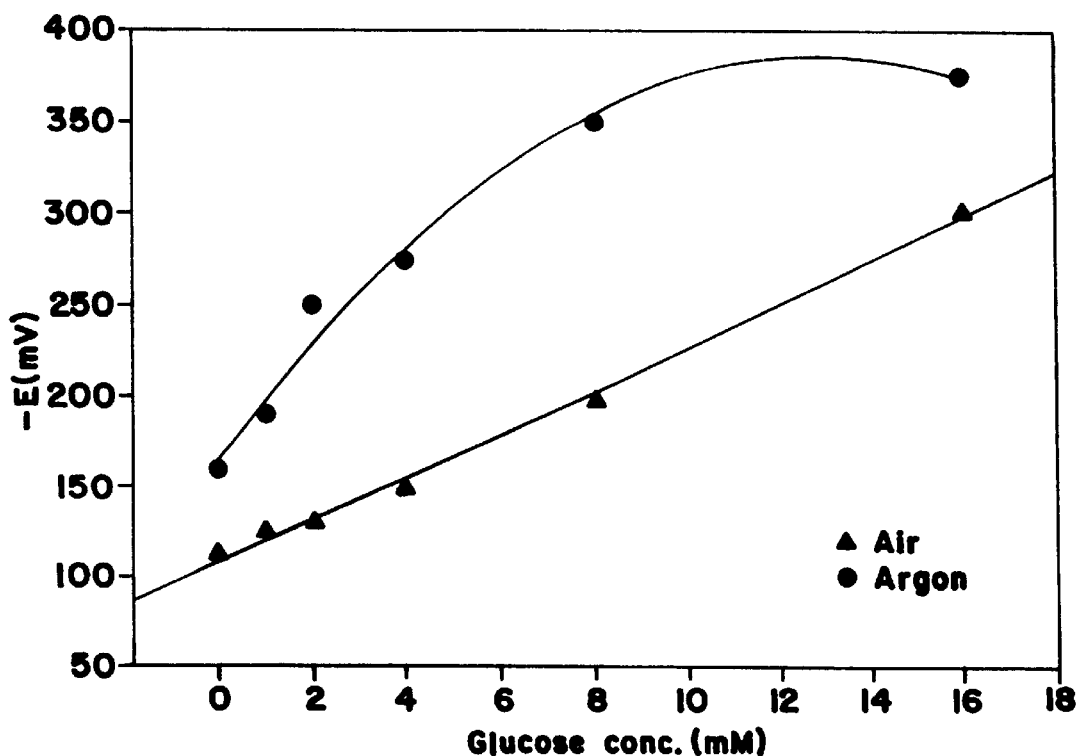
FIG. 7 is a graph showing the effect of deoxygenation of the solution on the potentiometric calibration curve. Conditions and the electrode were as described above for FIG. 6; with potential pulses applied for t=1 second.

FIG. 6 shows the dependence of the potential difference (absolute value vs. ground) on the glucose concentration. The potential was measured after the electrode was poised at 300 mV (Ag/AgCl) for 1, 2 or 5 seconds (switch closed) then allowed to float for 50 seconds (switch opened). The values obtained for 1, 2 or 5 seconds pulses were similar, the potential decreasing linearly with glucose concentration. The effect of de-oxygeneration on the potentiometric calibration curve is shown in FIG. 7. The effects of de-oxygenation on the potentiometric and amperometric calibration curves were similar (FIG. 4). The relationship between the measured currents and potentials is shown in FIG. 8. The potentials varied linearly with the currents, both in air and under argon.

Example 4

Potentiometric Analyte Electrodes

To establish that the apparently linear dependence of the potential on the current was not unique to the 0.25 mm diameter recessed gold electrode, the interdependences of the potential, current and glucose concentrations were determined also for a 5 mm diameter printer carbon electrode on Mylar™ with a sensing layer identical with that of the miniature gold electrode but with a Poretics® polycarbonate membrane. Although the structure, size and mass transport restricting membranes were quite different for the two electrodes, the results were similar, their potentials varied linearly with glucose concentration (FIG. 9).

Example 5

No Linear Dependence Without Resistant Film

Figure 10A:
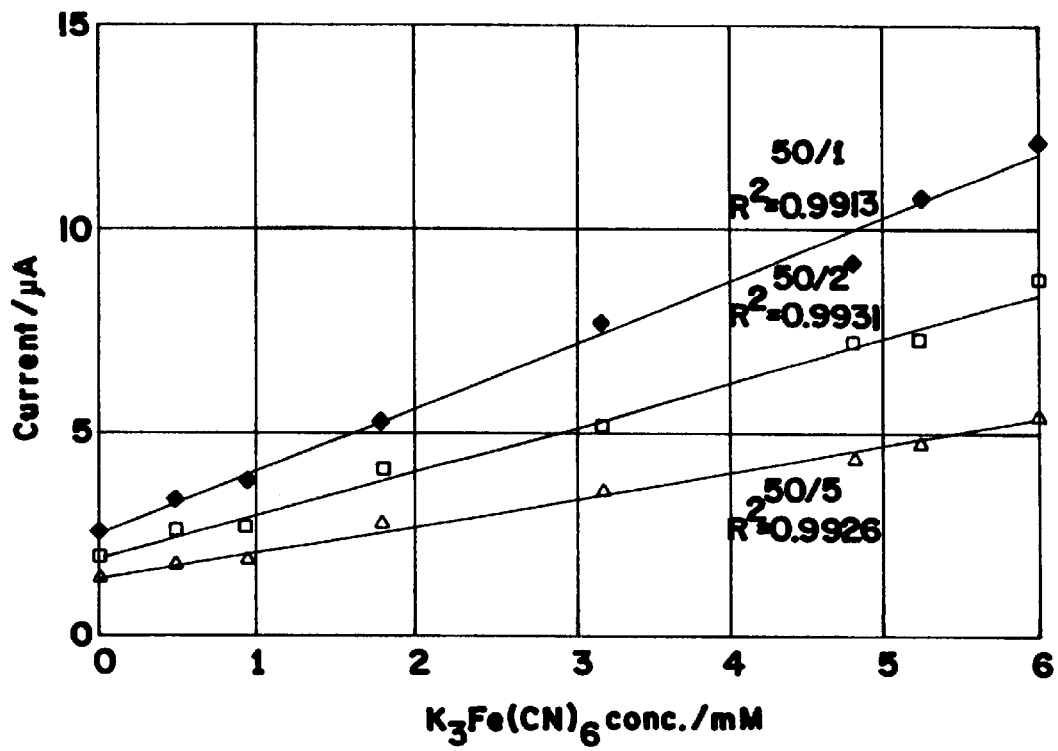
FIGS. 10A and 10B are graphs showing the dependence of the current (FIG. 10A) and of the potential (FIG. 10B) on a concentration of $K_3Fe(CN)_6$. τ=50 seconds; t=1 second; 100, 200 and 300 mV potential pulses. A 3 mm diameter platinum electrode was used.
Figure 10B:
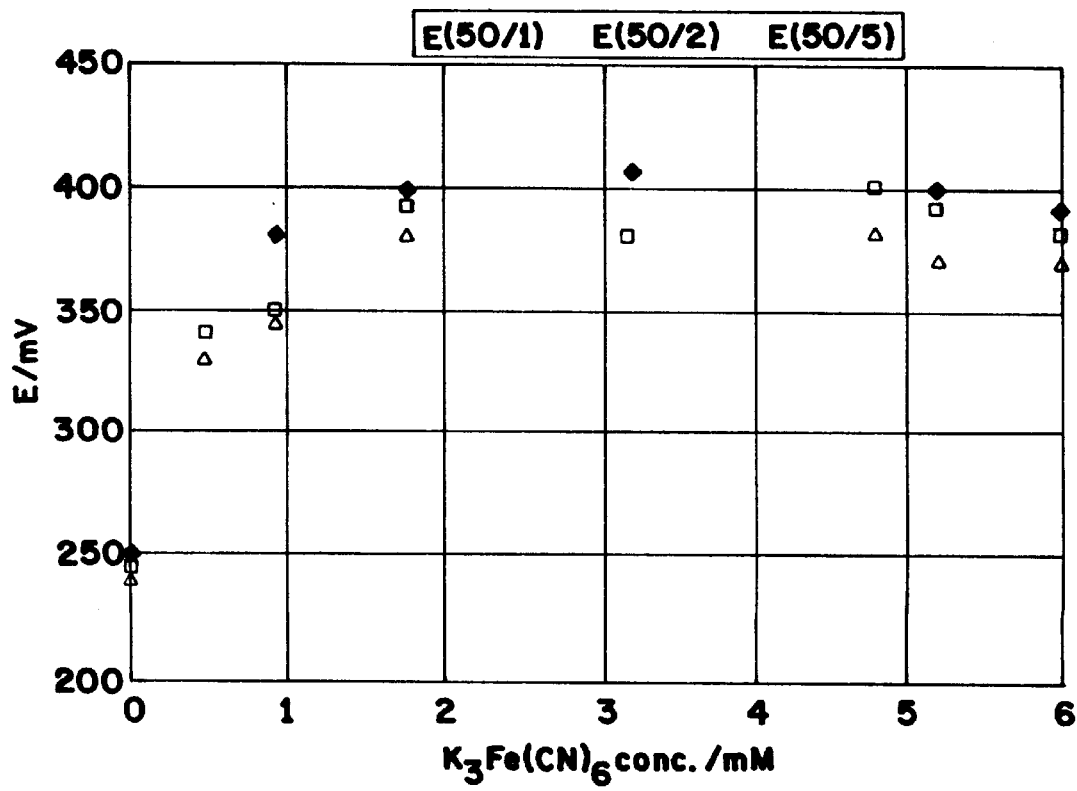

The experiments of FIG. 10 show, for comparison, the behavior of a conventional 3 mm diameter platinum electrode, to which a redox polymer film was not applied, in $K_3Fe(CN)_6$ solutions of different concentrations. Figure 10A shows the dependence of the current, measured at the end of $\tau$=1 second 100, 200 or 300 mV (Ag/AgCl) potential pulses, on the concentration of $K_3Fe(CN)_6$; FIG. 10B shows the potentials at the end the t=50 seconds open circuit potential periods. Here the potential does not vary linearly with the concentration of $K_3Fe(CN)_6$.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. The claims are intended to cover such modifications and devices.

All of the publications and patent applications in this specification are indicative of the level of ordinary skill in the art to which this invention pertains. All publications and patent applications are herein incorporated by reference to the same extent as if each individual publication or patent application was specifically and individually indicated by reference.

We claim:

1. A method for determining a concentration of an analyte, comprising:

contacting a working electrode with the analyte;
applying a first potential at the working electrode to electroreduce or electrooxidize a plurality of redox centers disposed in a conductive film on the working electrode;
removing the first potential;
electrooxidizing or electroreducing the redox centers using the analyte as reductant or oxidant;
measuring a second potential at the working electrode after removing the first potential; and
correlating the second potential approximately linearly with the concentration of the analyte.

2. The method of claim 1, wherein the conductive film further includes a polymer.

3. The method of claim 2, wherein the redox centers are ionically, covalently, or coordinatively bound to the polymer.

4. The method of claim 1, wherein the diffusivity of electrons through the conductive film immersed in an aqueous ionic solution ranges from $10^{-5}$ to $10^{-12}$ $cm^2sec^{-1}$.

5. The method of claim 1, wherein removing the first potential comprises operating a switch to decouple a potential-producing device from the working electrode.

6. The method of claim 5, wherein operating a switch comprises opening a switch according to a signal from a timer coupled to the switch.

7. The method of claim 1, wherein correlating a second potential comprises observing a potential of the working electrode, after removing the first potential, until a steady second potential is achieved.

8. The method of claim 7, wherein observing a potential of the working electrode comprises observing the potential of the working electrode, after removing the first potential, until the difference between an asymptotically approached potential and the observed potential equals, or is smaller than, a difference that would produce an error in an analyte concentration that is smaller than a desired percentage or absolute value of the concentration.

9. The method of claim 1, wherein applying a first potential comprises coupling the working electrode to a potentiostat to provide the first potential.

10. The method of claim 1, wherein electrooxidizing or electroreducing the redox centers using the analyte comprises electrooxidizing or electroreducing the redox centers in the presence of an enzyme that catalyzes an electrolytic reaction of the redox centers with the analyte.

11. An analyte sensing system comprising:
a working electrode;
a film disposed on the working electrode and having a plurality of redox centers to transfer electrons between the analyte and the working electrode;
a potential-producing device that, when connected to the working electrode, provides a first potential at the working electrode to electroreduce or electrooxidize the redox centers; a switch disposed between the working electrode and the potential-producing device to connect and disconnect the potential-producing device from the working electrode to apply or remove, respectively, the first potential at the working electrode, wherein, when the first potential is removed from the working electrode, a second potential is achieved at the working electrode as the analyte electrooxidizes or electroreduces the redox centers; and
a detector for measuring the second potential and correlating the second potential to a concentration of the analyte, wherein the analyte sensing system is configured to produce a second potential that varies approximately linearly with the concentration of the analyte.

12. The analyte sensing system of claim 11, wherein the film further comprises a polymer.

13. The analyte sensing system of claim 12, wherein the redox centers are ionically, covalently, or coordinatively bound to the polymer.

14. The analyte sensing system of claim 11, further comprising an enzyme disposed on the working electrode, wherein the enzyme catalyzes an electrolytic reaction of the analyte with the redox centers.

15. The analyte sensing system of claim 14, wherein the enzyme is disposed in the film.

16. The analyte sensing system of claim 11, wherein the analyte is glucose.

17. The analyte sensing system of claim 11, wherein the diffusivity of electrons through the film immersed in an aqueous ionic solution ranges from $10^{-5}$ to $10^{-12}$ $cm^2sec^{-1}$.

18. The analyte sensing system of claim 11; wherein the switch comprises an analog switch, a Hall effect switch, a reed switch, a transistor, or other semiconductor device or circuit.

19. An analyte sensing system comprising:
a working electrode;
a film disposed on the working electrode and having a plurality of redox centers to transfer electrons between the analyte and the working electrode;
a means for generating a first potential at the working electrode to electroreduce or electrooxidize the redox centers;
a means for decoupling the first potential from the working electrode, wherein, when the first potential is decoupled from the working electrode, the analyte electrooxidizes or electroreduces the redox centers to achieve a second potential that varies with analyte concentration; and
a means for measuring the second potential and correlating approximately linearly the second potential to the analyte concentration.

20. The analyte sensing system of claim 19, wherein the means for generating a first potential comprises a potentiostat.

21. The analyte sensing system of claim 19, wherein the means for decoupling the first potential from the working electrode comprises an analog switch, a Hall effect switch, a reed switch, a transistor, or other semiconductor device or circuit.

22. A method of measuring an analyte concentration, the method comprising steps of:
measuring a potential between a working electrode and a reference electrode, the working electrode having redox centers and an analyte-responsive catalyst disposed on the working electrode; and
correlating the potential to the analyte concentration, wherein the potential varies linearly with analyte concentration over a range of the analyte concentration.

23. The method of claim 22, wherein the analyte comprises glucose.

24. The method of claim 23, wherein the potential varies linearly with glucose concentration over 0 to 5 mM glucose.

25. The method of claim 23, wherein the potential varies linearly with glucose concentration over 0 to 10 mM glucose.

26. The method of claim 25, wherein the potential varies by at least 10 mV/mM glucose over 0 to 10 mM glucose.

* * * * *

UNITED STATES PATENT AND TRADEMARK OFFICE
CERTIFICATE OF CORRECTION

PATENT NO. : 6,251,260 B1
DATED : June 26, 2001
INVENTOR(S) : Heller et al.

Page 1 of 1

It is certified that error appears in the above-identified patent and that said Letters Patent is hereby corrected as shown below:

<u>Title page,</u>
Item [54], Title, "ANALYTIC" should read -- ANALYTE --.
Item [56], References Cited, U.S. PATENT DOCUMENTS, "4,924,516" should read -- 4,927,516 --

<u>Column 2,</u>
Line 61, insert -- $\propto$ -- after "I"

<u>Column 8,</u>
Line 3, insert -- $\propto$ -- after "logI"

Signed and Sealed this

Thirtieth Day of April, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,251,260 B1
APPLICATION NO. : 09/158973
DATED : June 26, 2001
INVENTOR(S) : Adam Heller and Chaim Yarnitzky It is certified that error appears in the above-identified patent and that said Letters Patent is hereby corrected as shown below:

In the Specification

Column 1, line 3, above the FIELD OF THE INVENTION section, please insert the following:

--STATEMENT REGARDING FEDERALLY SPONSORED RESEARCH

This invention was made with government support under Grant no. DK042015 awarded by the National Institutes of Health; and 9505956 awarded by the National Science Foundation. The government has certain rights in the invention.--

Signed and Sealed this
Second Day of June, 2015

Michelle K. Lee
*Director of the United States Patent and Trademark Office*